(12) United States Patent
Terada et al.

(10) Patent No.: US 8,369,939 B2
(45) Date of Patent: Feb. 5, 2013

(54) ACTIVATION APPARATUS, METHOD, AND COMPUTER PROGRAM FOR BRAINWAVE INTERFACE SYSTEM

(75) Inventors: Yoshihisa Terada, Osaka (JP); Shinobu Adachi, Osaka (JP); Koji Morikawa, Kyoto (JP)

(73) Assignee: Panasonic Corporation, Osaka (JP)

(*) Notice: Subject to any disclaimer, the term of this patent is extended or adjusted under 35 U.S.C. 154(b) by 894 days.

(21) Appl. No.: 12/447,718

(22) PCT Filed: Oct. 21, 2008

(86) PCT No.: PCT/JP2008/002977
§ 371 (c)(1),
(2), (4) Date: Apr. 29, 2009

(87) PCT Pub. No.: WO2009/057260
PCT Pub. Date: May 7, 2009

(65) Prior Publication Data
US 2010/0317988 A1 Dec. 16, 2010

(30) Foreign Application Priority Data
Oct. 29, 2007 (JP) .................. 2007-280895

(51) Int. Cl.
*A61B 5/04* (2006.01)
(52) U.S. Cl. ........................ 600/544; 600/545
(58) Field of Classification Search .................. 600/544, 600/545
See application file for complete search history.

(56) References Cited

U.S. PATENT DOCUMENTS 4,926,969 A * 5/1990 Wright et al. ................. 600/544

(Continued)

FOREIGN PATENT DOCUMENTS

| JP | 10-033513 | 2/1998 |
|----|-----------|--------|
| JP | 11-073286 | 3/1999 |

(Continued)

OTHER PUBLICATIONS

"P200." Wikipedia.org (http://en.wikipedia.org/wiki/P200).*

(Continued)

*Primary Examiner* — Patricia Mallari
*Assistant Examiner* — Tiffany Weston
(74) *Attorney, Agent, or Firm* — Renner, Otto, Boisselle & Sklar, LLP

(57) ABSTRACT

An electroencephalogram IF system includes an electroencephalogram measurement section for measuring an electroencephalogram signal, a function control section for analyzing an event-related potential contained in the electroencephalogram signal and outputting a function control signal for controlling a function of a device based on the result of analysis, and an output section for outputting the function control signal. The activation apparatus includes: an activation determination section for, while the electroencephalogram IF system is not functioning, transmitting to the output section a stimulation control signal for controlling presentation and vanishing of a visual stimulation on a single-item on the output section and, within the electroencephalogram signal acquired from the electroencephalogram measurement section, allowing a P200 component value of an event-related potential since the timing of presenting the visual stimulation as a starting point to be compared against a predetermined threshold value, and determining whether or not to output an activation trigger to the function control section based on the result of comparison; and a stimulation attention determination section for determining whether or not the user is paying attention to the visual stimulation based on an N100 component of the event-related potential since the timing of presenting the visual stimulation as a starting point, and causing processing by the activation determination section to begin depending on the determination result. When the activation determination section outputs an activation trigger, the electroencephalogram IF system is activated.

12 Claims, 20 Drawing Sheets

U.S. PATENT DOCUMENTS

2003/0013981 A1* 1/2003 Gevins et al. .............. 600/544
2005/0017870 A1* 1/2005 Allison et al. ........... 340/825.19

FOREIGN PATENT DOCUMENTS

| JP | 11-123181 | 5/1999 |
| JP | 11-203022 | 7/1999 |
| JP | 2000-075991 | 3/2000 |
| JP | 2004-086768 | 3/2004 |
| JP | 2005-034620 | 3/2004 |

OTHER PUBLICATIONS

International Search Report for corresponding application No. PCT/JP2008/002977 mailed Nov. 18, 2008.

Emanuel Donchin et al.; "The Mental Prosthesis: Assessing the Speed of a P300-Based Brain-Computer Interface"; IEEE, Transactions on Rehabilitation Engineering, vol. 8, No. 2, Jun. 2000, pp. 174-179.

Kimitaka Kaga et al.; "Event-Related Potential (ERP) Manual—mainly concerning P300"; Shinohara Shuppan Shinsha, 1995 and a partial English translation.

Madoka Takahara et al.; "Comparison of the event-related potentials between REM sleep and the sleep onset period"; Hiroshima University, Faculty of Integrated Arts and Sciences, Transactions IV, Scientific Faculties, vol. 28, Dec. 2002, pp. 1-11.

Form PCT/ISA/237 and partial English Translation.

Notice for Reasons for Rejection for corresponding Japanese Application No. 2009-510224 dated Jun. 23, 2009 (with translation).

Naomi Terada et al., "Communication Aid using ERP on the Single Trial"; general lectures from FIT2002, vol. 3, The Institute of Electronics, Information and Communication Engineers, Sep. 13, 2002, pp. 465-466.

* cited by examiner (a) SCREEN BEFORE SELECTION
(b) MENU ITEM SCREEN
(c) EVENT-RELATED POTENTIAL SINCE SWITCHING OF MENU ITEM AS A STARTING POINT
(d) SCREEN AFTER SELECTION FIG.15
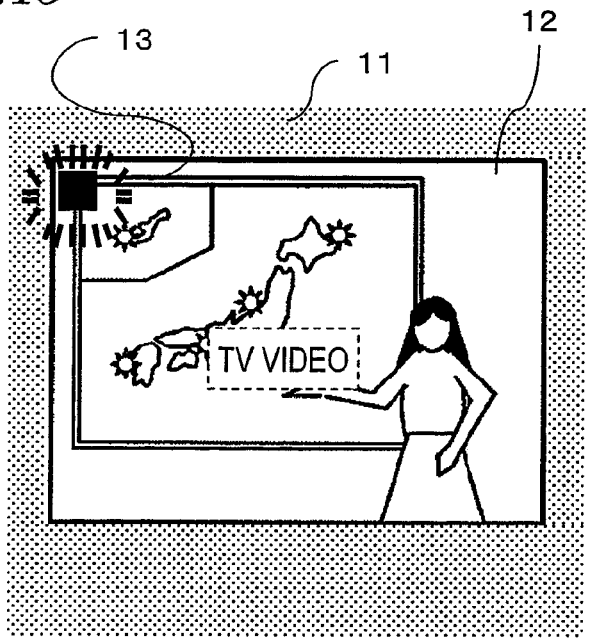
(a)
WHEN ICON IS NOT WATCHED
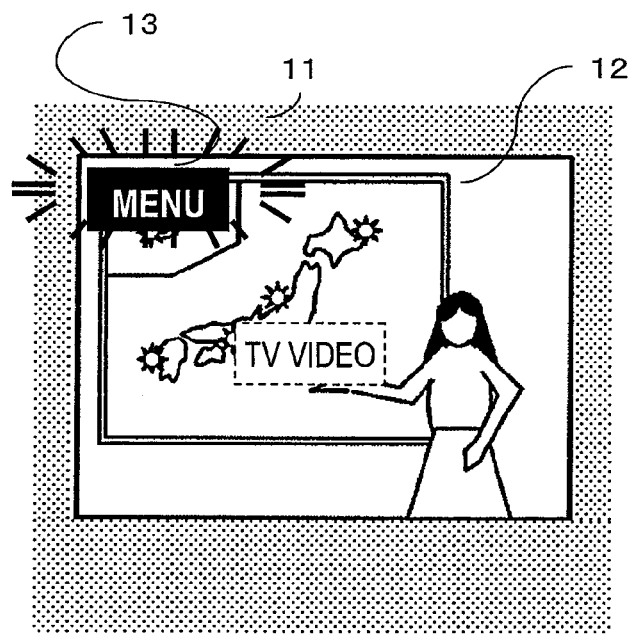
(b)
WHEN ICON IS WATCHED

| PATTERN | OBJECT NAME | OPERATING FUNCTION |
|---|---|---|
| ☺ | NIKONIKO-MART | DISPLAY MAP OF NEAREST STORES |
| 🚫 | DELICIOUS-RESTAURANT | DISPLAY DISCOUNT COUPON |
| — | PUSH BUTTON AT CROSSWALK | SWITCH TO "WAIT" |
| ⋮ | ⋮ | ⋮ |

| DEVICE NAME | DEVICE 1 (ELECTROMAGNETIC COOKER 141a) | DEVICE 2 (MICROWAVE OVEN 141b) | ... | DEVICE n (VENTILATION FAN 141n) |
|---|---|---|---|---|
| LIGHTING START TIME | 12:01:30.000 | 12:01:31.000 | | 12:01:31.500 |
| LIGHTING PERIOD | 600ms | 1400ms | ... | 1000ms |
| DEVICE OPERATION | HEATING | START WARMING | ... | On/Off |

ACTIVATION APPARATUS, METHOD, AND COMPUTER PROGRAM FOR BRAINWAVE INTERFACE SYSTEM

TECHNICAL FIELD

The present invention relates to an interface with which devices are manipulated by utilizing an electroencephalogram (electroencephalogram interface system). More specifically, the present invention relates to an activation apparatus which is incorporated in an electroencephalogram interface system for selecting and activating a desired function by utilizing the electroencephalogram of a user, an activation method, and a computer program which is executed on such an activation apparatus.

BACKGROUND ART

Various devices have been proposed in our lives. While living among such devices, users enjoy desired information or services by manipulating the devices. Because of an increase in the number of devices themselves, an increase in the information that cannot be obtained without using devices, and so on, the importance of improving the manipulability of such interfaces is increasing year after year. In information devices (television sets, mobile phones, PDAs, etc.), for example, device manipulations are hitherto realized by selecting an manipulation option while watching a screen. As manipulation input means thereof, methods such as pressing a button, moving a cursor and making a confirmation, or manipulating a mouse while watching a screen have been used. However, it has been difficult to execute a manipulation when both hands are unavailable, due to tasks other than device manipulations, e.g., household chores, rearing of children, and driving an automobile.

In answer thereto, there are input means utilizing biometric signals from a user. Non-Patent Document 1 discloses a technique that utilizes an event-related potential of an electroencephalogram for distinguishing an option which a user wishes to select.

Specifically, options are randomly highlighted, and a positive component (P300 component) which appears in a time slot from 300 ms to 500 ms after a point in time that an option that the user wishes to select was highlighted is utilized to enable distinction as to wishing to select or not. According to this technique, even in a situation where both hands are full, or even in a situation where the user is unable to move his or her limbs due to an illness or the like, the user can select an option which they wish to select, whereby an interface for device manipulations, etc., can be realized.

Thus, conventionally, a menu selection based on an electroencephalogram has been realized by applying various processing to an electroencephalogram signal.

[Non-Patent Document 1] Emanuel Donchin and two others, "The Mental Prosthesis: Assessing the Speed of a P300-Based Brain-Computer Interface", IEEE TRANSACTIONS ON REHABILITATION ENGINEERING, Vol. 8, No. 2, June 2000

DISCLOSURE OF INVENTION

Problems to be Solved by the Invention

However, in the aforementioned instances of electroencephalogram interfaces, only a selection from among options is discussed, and there is no discussion of how an electroencephalogram interface is activated. The reason is that, these instances envisage use in a situation where a screen of an electroencephalogram interface (e.g., an option presenting screen) is always displayed. When an electroencephalogram interface is used for a person in a hospital who is having difficulties with his or her body, for example, a screen of an electroencephalogram interface (e.g., an option presenting screen) has always been displayed by the bedside.

On the other hand, when mounted on an information device in daily life, a screen of the information terminal is occupied with information which is meant to be presented by the natural function of the information terminal, e.g., schedule, main text of mail, or a TV program, and thus it is not possible to always display a screen of an electroencephalogram interface. Thus, a step is required which can activate an electroencephalogram interface without obstructing the information such as TV video that is presented by the natural role of the information terminal.

It might be possible to provide an activation button for causing a screen of an electroencephalogram interface to be displayed. However, in situations where both hands are full because of tasks other than a device manipulation, e.g. household chores, rearing of children, or driving, it is difficult to use an electroencephalogram interface. In view of the users' need to manipulate an information device in every kind of situation by using an electroencephalogram interface, it is necessary to achieve its activation also by using an electroencephalogram.

An objective of the present invention is to realize even an activation of an electroencephalogram interface through the use of a biological signal (electroencephalogram signal) from a user.

Means for Solving the Problems

An apparatus according to the present invention is an activation apparatus for activating an electroencephalogram interface system, the electroencephalogram interface system including an electroencephalogram measurement section for measuring an electroencephalogram signal from a user, a function control section for analyzing an event-related potential contained in the electroencephalogram signal and outputting a function control signal for controlling a function of a device based on a result of analysis, and an output section for outputting the function control signal, the activation apparatus comprising: an activation determination section for, while the electroencephalogram interface system is not functioning, transmitting to the output section a stimulation control signal for controlling presentation and vanishing of a visual stimulation on a single-item on the output section, and, within the electroencephalogram signal acquired from the electroencephalogram measurement section, allowing a P200 component value of an event-related potential since a timing of presenting the visual stimulation as a starting point to be compared against a predetermined threshold value, and determining whether or not to output an activation trigger to the function control section based on a result of comparison; and a stimulation attention determination section for determining whether or not the user is paying attention to the visual stimulation based on an N100 component of the event-related potential since the timing of presenting the visual stimulation as a starting point, and causing processing by the activation determination section to begin depending on a determination result. The activation apparatus activates the electroencephalogram interface system by outputting the activation trigger.

As the P200 component value, the activation determination section may compare a value of the event-related potential in a zone of 200±50 ms since the timing of presenting the visual stimulation as a starting point against the predetermined threshold value.

As the P200 component value, the activation determination section may compare a local maximum value, a maximum value, or a zone average value of the event-related potential in a zone of 200±50 ms since the timing of presenting the visual stimulation as a starting point against the predetermined threshold value.

The stimulation attention determination section may instruct the activation determination section to change a method of presenting the visual stimulation based on a determination result that the user is paying attention to the visual stimulation.

The electroencephalogram interface system may include an imaging device for imaging a video and outputting a video signal; the activation apparatus may further comprise a flicker detection section for detecting based on the video signal a subject which is flickering in the video, and based on a characteristic quantity of the subject, generating function control information which designates a function to be executed by the function control section, and outputting information indicating a lighting timing of the subject and the function control information; the activation determination section may identify a timing of presenting the visual stimulation based on the information indicating the lighting timing, and when outputting an activation trigger to the function control section, output a control signal based on the function control information; and the function control section of the electroencephalogram interface system may execute a specific function based on the activation trigger and the function control information.

The flicker detection section may retain a database defining a correspondence between characteristic quantities of subjects and functions to be executed by the function control section, and by recognizing a characteristic quantity of the subject and referring to the database based on the characteristic quantity, identify a function to be executed by the function control section and output the function control information.

In an electroencephalogram interface system having an electroencephalogram measurement section for measuring an electroencephalogram signal from a user and a plurality of devices, an activation apparatus for activating at least one of the plurality of devices, each of the plurality of devices including a function control section for outputting a function control signal for controlling a function of the device and an output section for outputting the function control signal; the activation apparatus comprising: a flicker timing control section for controlling the output section of each device to repeat presentation and vanishing of a visual stimulation, and outputting a determination trigger indicating a timing with which the visual stimulation is presented at any of the devices; a storage medium for retaining determination trigger information identifying a timing of outputting the determination trigger and a device that is presenting the visual stimulation when the determination trigger is output; and an activation determination section for, within the electroencephalogram signal acquired from the electroencephalogram measurement section, allowing a P200 component value of an event-related potential since a timing of receiving the determination trigger as a starting point to be compared against a predetermined threshold value, and based on a result of comparison, identifying the device presenting the visual stimulation based on the timing of receiving the determination trigger and the determination trigger information, and outputting an activation trigger to the function control section of the identified device. The activation apparatus may activate the device identified by the activation determination section by outputting the activation trigger.

A method according to the present invention is an activation method for activating an electroencephalogram interface system, the electroencephalogram interface system including an electroencephalogram measurement section for measuring an electroencephalogram signal from a user, a function control section for analyzing an event-related potential contained in the electroencephalogram signal and outputting a function control signal for controlling a function of a device based on a result of analysis, and an output section for outputting the function control signal, the activation method comprising the steps of: while the electroencephalogram interface system is not functioning, transmitting to the output section a stimulation control signal for controlling presentation and vanishing of a visual stimulation on a single-item on the output section; determining whether or not the user is paying attention to the visual stimulation based on an N100 component of the event-related potential since a timing of presenting the visual stimulation as a starting point; based on a determination result, allowing a P200 component value of an event-related potential since the timing of presenting the visual stimulation as a starting point, within the electroencephalogram signal acquired from the electroencephalogram measurement section, to be compared against a predetermined threshold value; determining whether or not to output an activation trigger to the function control section based on a result of comparison; and activating the electroencephalogram interface system by outputting the activation trigger when it is determined to output the activation trigger.

A computer program is a computer program to be executed in an activation apparatus incorporated in an electroencephalogram interface system, the electroencephalogram interface system including an electroencephalogram measurement section for measuring an electroencephalogram signal from a user, a function control section for analyzing an event-related potential contained in the electroencephalogram signal and outputting a function control signal for controlling a function of a device based on a result of analysis, and an output section for outputting the function control signal, wherein, the computer program causes a computer of the activation apparatus to execute: while the electroencephalogram interface system is not functioning, transmitting to the output section a stimulation control signal for controlling presentation and vanishing of a visual stimulation on a single-item on the output section; determining whether or not the user is paying attention to the visual stimulation based on an N100 component of the event-related potential since a timing of presenting the visual stimulation as a starting point; based on a determination result, allowing a P200 component value of an event-related potential since the timing of presenting the visual stimulation as a starting point, within the electroencephalogram signal acquired from the electroencephalogram measurement section, to be compared against a predetermined threshold value; determining whether or not to output an activation trigger to the function control section based on a result of comparison; and activating the electroencephalogram interface system by outputting the activation trigger when it is determined to output the activation trigger.

Effects of the Invention

With an electroencephalogram interface system according to the present invention, a visual stimulation for activation of an electroencephalogram interface (an icon on a screen, an LED, etc.) is flickered, and it is first determined whether a user is paying attention to the visual stimulation, based on an N100 component of an event-related potential since the timing of presenting the visual stimulation as a starting point. Then, based on the determination result (specifically, when it is determined that the user is paying attention to the visual stimulation), the user's will of activation is determined based on whether a P200 component of an event-related potential since the timing of presenting the visual stimulation for activation as a starting point is appearing in the electroencephalogram or not. If this component is appearing in the electroencephalogram, the electroencephalogram interface is activated.

As a result, in a situation where both hands are unavailable due to tasks other than device manipulations, e.g., household chores, rearing of children, or driving an automobile, for example, it is possible to activate an electroencephalogram interface with the timing as desired by the user, without performing any physical manipulations such as pressing a button.

BRIEF DESCRIPTION OF DRAWINGS

FIG. 15 (a) is a diagram showing an icon 13 when it is determined that the user 2 is not watching the icon 13; and (b) is a diagram showing the icon 13 displayed in an enlarged size when it is determined that the user 2 is watching the icon 13.

Figure 1:
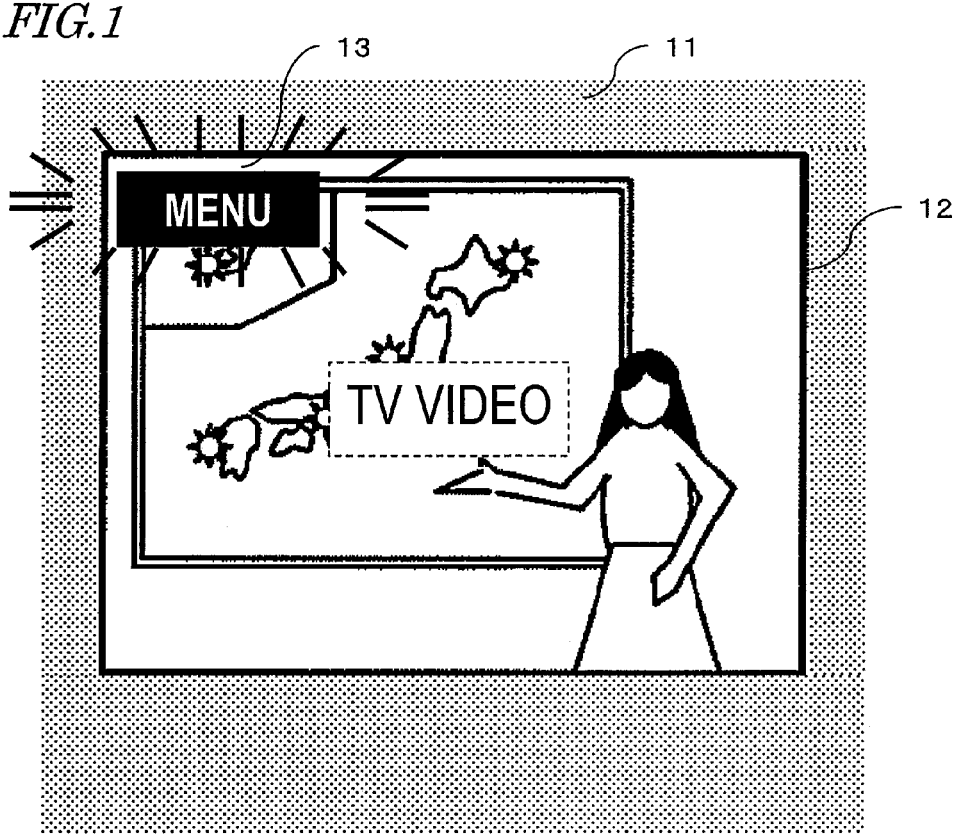
FIG. 1 A diagram showing an exemplary TV screen of an electroencephalogram activation interface.

DESCRIPTION OF REFERENCE NUMERALS 1 electroencephalogram interface system
2 user
3 electroencephalogram measurement section
4 activation determination section
5 function control section
6 output section
7 stimulation attention determination section
8 flicker timing control section
9 flicker detection section
20, 21, 22, 195 activation apparatus

BEST MODE FOR CARRYING OUT THE INVENTION

First, the points which the inventors have studied concerning the aforementioned problems will be described.

In order to realize activation of an electroencephalogram interface system based on an electroencephalogram, the inventors have conceived a method of giving a visual stimulation to a user and utilizing an event-related potential immediately after the presentation of the visual stimulation. As the visual stimulation, an option (activation icon) for electroencephalogram interface activation is constantly flickered in a portion of an information presentation screen. If the user wishes to activate an electroencephalogram interface, he or she inwardly thinks "I want to activate it" or "That", in accordance with the timing that the activation icon was lit. According to the concept of Non-Patent Document 1, it is supposed possible to determine a user's will of activation, by utilizing the P300 component of an event-related potential since the lighting of the icon as a starting point.

Based on the above study, an experiment was performed to measure an event-related potential responsive to a flickering stimulation of an icon which was displayed on a TV screen (the details thereof will be described later). It was found through the experiment that, even when the user has a will of activation, it does not always follow that a clear peak of positive component of an event-related potential will appear between 300 ms to 400 ms since the lighting of the icon as a starting point, and thus, determination of a will of activation by utilizing the P300 component may not be possible.

This is considered because, in the case of an activation, there is one stimulation with a monotonous presentation interval, unlike in the case of a "selection" where one option is chosen from among a plurality of options; therefore, since the user is able to anticipate the timing of the stimulation, the component which would be utilized for a "selection" is not available.

Accordingly, through a further analysis of the waveform of the measured event-related potential, it was found that the event-related potential is characterized by an N100 component, which is the amplitude value of a negative peak (local minimum value) that occurs in a zone of 50 ms before and after 100 ms since the lighting of the icon as a starting point (100±50 ms), and a P200 component, which is the amplitude value of a positive peak (local maximum value) that occurs in a zone of 50 ms before and after 200 ms (200±50 ms)(the details thereof will be described later).

In conventional studies, e.g., a document concerning measurement of the efficacy of sedative sleeping pills (Japanese Laid-Open Patent Publication No. 10-33513), the P200 component is explained as a response in the case where "the pain of a stimulation or the like is recognized as a sensation". Moreover, according to a study concerning comparative responses to a surgeon's stimulation during arousal/REM sleep/hypnagogic periods ("COMPARISION OF THE EVENT-RELATED POTENTIALS BETWEEN REM SLEEP AND THE SLEEP ONSET PERIOD", Takahara et al., Hiroshima University, Faculty of Integrated Arts and Sciences, Transactions IV, Scientific Faculties, vol. 28, pp. 1-11, December 2002), the P200 component was being recognized as a "response to an audio stimulation during REM sleep". Thus, the P200 component is a signal which has not been utilized at all for purposes concerning "determination of a will of activation" and "determination of a will to select a certain item".

One technique concerning an electroencephalogram interface utilizing an electroencephalographic characteristic signal is a technique described in "METHOD AND APPARATUS OF DETERMINATION OF PSYCHOLOGICAL STATE AND LIKE OF HUMAN BY USING EVENT-RELATED POTENTIAL" (Japanese Laid-Open Patent Publication No. 2005-034620). This document mentions selection of an option which is desired by a user (target word) by utilizing a P200 component or a P300 component according to the characteristics of an individual, but does not take into consideration a P200 component when watching TV, which is a different situation from selecting a target word.

However, the inventors have found through the following experiment that, by utilizing the N100 component and the P200 component, it is possible to determine a will of activation of a user who is watching TV. Hereinafter, particulars of the experiment by the inventors will be described in detail.

The inventors have conducted an experiment to verify whether the aforementioned technique is applicable or not by utilizing a TV screen. In this experiment, it was contemplated that an activation apparatus for activating an electroencephalogram interface system was incorporated in a TV. Specifically, an icon in a TV screen was flickered, and the characteristic features of a user's electroencephalogram when the user had a will of activation were extracted.

FIG. 1 shows an exemplary TV screen of an electroencephalogram activation interface. TV video is displayed on a TV screen 12 of a TV set 11, and an icon 13 for electroencephalogram interface activation was flickered with a constant period in an upper left portion of the TV screen 12. The icon 13 was flickered so that it was lit for 700 ms and extinguished for 700 ms, this being repeated. The site of electroencephalogram measurement was the user's parietal (Pz in the International 10-20 system), and the measurement was taken on the basis of the posterior of the right ear (mastoid) as a reference. Furthermore, a 15 Hz low-pass filter was utilized to remove noise components such as the source power. An event-related potential was cut out by defining the timing of lighting the icon as 0 ms, and a baseline correction was performed for −100 ms to 0 ms.

When the user wished to activate an electroencephalogram interface, i.e., he or she had a will of activation, the user was supposed to inwardly think "I want to activate it", "That", and so on, in accordance with the timing that the activation icon 13 was lit. Conversely, when activation was not desired, he or she was supposed to watch the TV video.

For two test subjects, event-related potentials of their electroencephalograms responsive to fifty icon flickers were measured, each under the three conditions of "(a) paying attention to the icon with a will of activation", "(b) looking at the icon without a will of activation", or "(c) watching TV video without a will of activation". Herein, in consideration of the fact that the P300 component of an event-related potential to appear at about 300 ms since the timing of icon lighting as a starting point is likely to occur at a point after 300 ms, a comparison of the respective waveforms of event-related potentials was performed in the zone from 300 ms to 500 ms.

Figure 2:
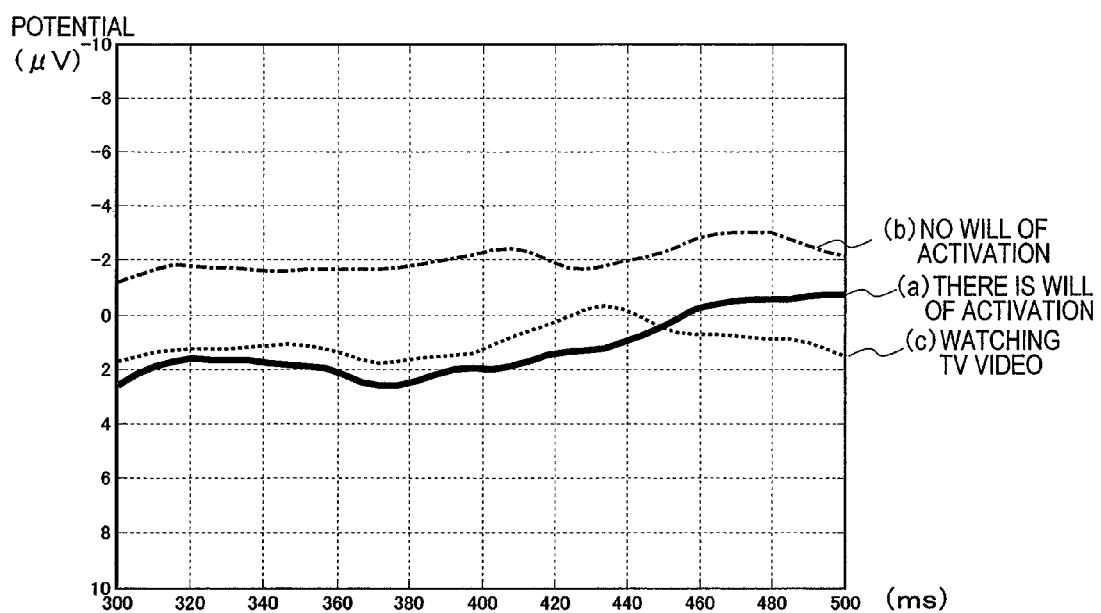
FIG. 2 A graph showing a result of comparison between the waveforms of event-related potentials measured under conditions (a), (b), and (c).

FIG. 2 shows a result of comparison between the waveforms of event-related potentials which were measured under conditions (a), (b), and (c). These waveforms are arithmetic means, in the zone from 300 ms to 500 ms zone, of all waveforms of event-related potentials since the timing that the icon was lit as a starting point, where the waveform under condition (a) is shown by a solid line, the waveform under condition (b) is shown by a chain line, and the waveform under condition (c) is shown by a dotted line.

According to FIG. 2, under all of conditions (a), (b), and (c), it is difficult to identify any clear peak of a positive component from 300 ms to 500 ms. Moreover, the ranges of values under conditions (a) and (c) are both from −1 to 2.5 μV, with a very small difference of 2 μV at the most between the two waveforms. Thus, it can be seen that, in the case of these test subjects, it is very difficult to determine the waveform of condition (a) "having a will of activation" through the use of the P300 component of the event-related potential.

Figure 3A:
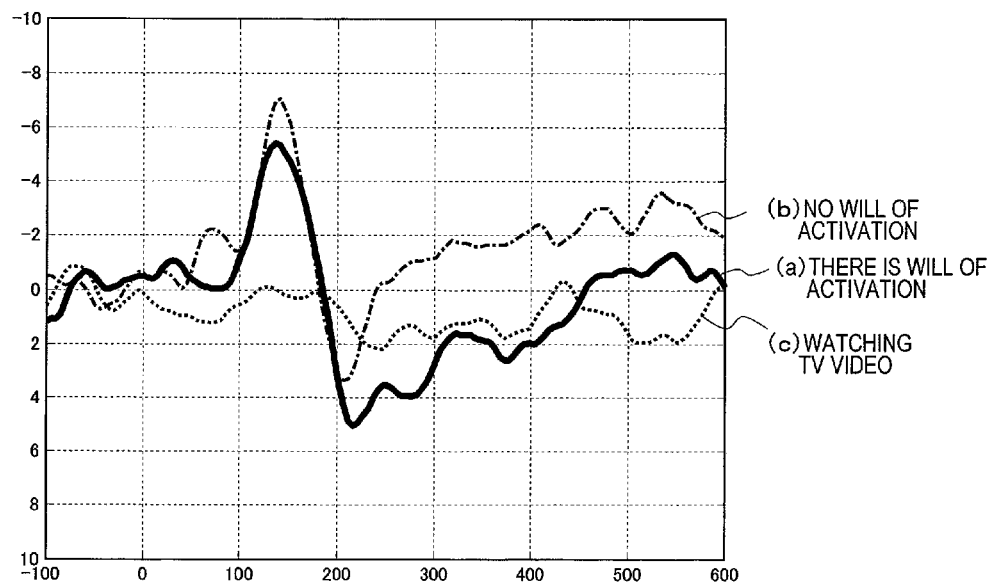
FIG. 3A A graph showing the waveforms of event-related potentials under conditions (a), (b), and (c).

Accordingly, the event-related potential in the entire zone from −100 ms to 600 ms when lighting an icon was analyzed. FIG. 3A shows the waveforms of event-related potentials under conditions (a), (b), and (c). Each graph is a waveform obtained from an arithmetic mean of 100 flickers (two test subjects×50 flickers). The waveform of condition (a) is shown by a solid line; the waveform of condition (b) is shown by a chain line; and the waveform of condition (c) is shown by a dotted line. Note that the waveform in the zone from 300 ms to 500 ms is the same as FIG. 2.

According to the waveform patterns of FIG. 3A, conditions (a) and (b) are both −4 µV or less. Thus, it can be seen that, in a zone of 50 ms before and after about 100 ms since the timing that the icon was lit as a starting point, the negative peak (local minimum value) (N100 component) has a large voltage value in the negative direction under condition (a) and condition (b). In other words, a negative peak with a large amplitude (i.e., N100 component) can be confirmed. Note that amplitude is a value to be expressed in an absolute value.

On the other hand, under condition (c), no large negative peak is observed in the aforementioned range, and even the minimum value is about 0 µV. Both of conditions (a) and (b) are states where the activation icon is being watched, whereas condition (c) is a state where the activation icon is not being looked at (watching TV video). Therefore, in a zone of 50 ms before and after about 100 ms since the timing that the icon was lit as a starting point, it is possible to determine whether the icon is being watched or not.

It can also be seen that the positive peak (local maximum value) occurring in a zone of 50 ms before and after about 200 ms has an amplitude value (P200 component) which is as high as about 5 µV under condition (a) of having a will of activation. Under condition (b) of having no will of activation, it is about 3 µV. Therefore, in a zone of 50 ms before and after about 200 ms since the timing that the icon was lit as a starting point, it is possible to determine whether there is a will of activation or not.

As described above, by determining watching of an activation icon based on the N100 component and by determining a will of activation based on the P200 component, it becomes possible to determine the three states of conditions (a), (b), and (c).

Figure 3B:
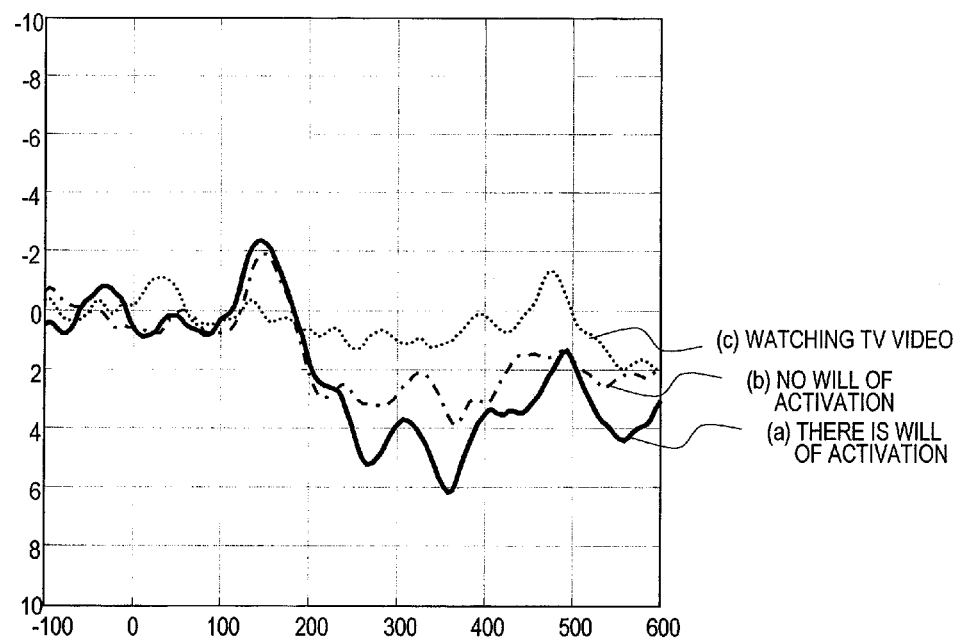
FIG. 3B A graph showing the waveforms of event-related potentials under conditions (a), (b), and (c), from test subjects that are different from the test subjects of FIG. 3A.

The inventors have conducted a similar experiment for 15 other test subjects. The results of the experiment are shown in FIG. 3B. From the results of FIG. 3B, it was confirmed that the N100 component and the P200 component are similarly appearing, and that the characteristic signal that distinguishes conditions (a), (b), and (c) is not specific to the above two test subjects, but is a commonly-appearing characteristic signal.

Accordingly, the inventors have decided to, by utilizing the N100 component of the P200 component of an event-related potential for the determination of a will of activation and allowing the N100 component and the P200 component while watching a flickering icon to be each compared against a reference value (threshold value), effectively control the flicker of the icon during TV watching and determine whether there is a will of activation or not, thus arriving at the present invention.

Hereinafter, with reference to the attached drawings, embodiments of the activation apparatus according to the present invention utilizing the above-described characteristic features will be described.

Note that, in the present specification, a point in time after the lapse of a predetermined time since a certain point in time is specifically identified in order to acquire an event-related potential; however, this point in time may span a certain breadth. Generally speaking, it is known that the waveform of an event-related potential may have differences (discrepancies) of 30 to 50 milliseconds from individual to individual (edited by Kimitaka KAGA et al., "Event-Related Potential (ERP) Manual—mainly concerning P300—", Shinohara Shuppan Shinsha, 1995; p. 30, Table 1). Therefore, the term "X milliseconds" can be considered as a representative value in the case where a breadth of "30 to 50 milliseconds" may exist before and after X milliseconds. Such a range may be explicitly encompassed by adding the term "about" or "neighborhood".

Embodiment 1

Hereinafter, the construction and operation of an activation apparatus for activating an electroencephalogram interface will be described.

Figure 4:
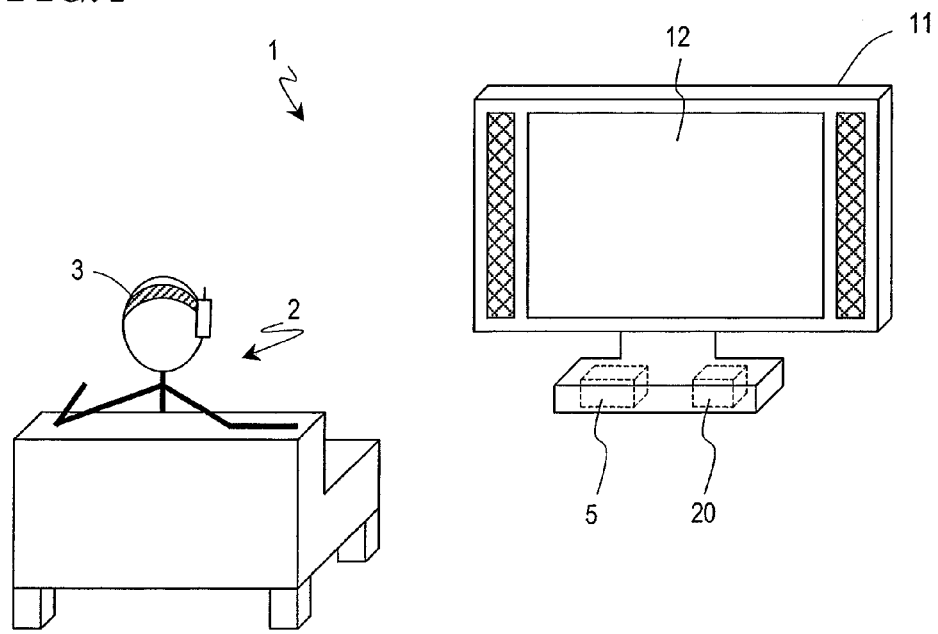
FIG. 4 A diagram showing a construction and an environment of use for an electroencephalogram interface system 1 according to the present embodiment.

FIG. 4 shows a construction and an environment of use for an electroencephalogram interface system 1 according to the present embodiment. In the present embodiment, the electroencephalogram interface system 1 includes an electroencephalogram measurement section 3 and a function control section 5.

The functions of the electroencephalogram interface system 1 will be generally described. First, an output section 6 causes a menu selection screen to be displayed on a TV screen 12, and the electroencephalogram measurement section 3 measures an electroencephalogram signal from a user 2. The function control section 5 analyzes an event-related potential contained in the measured electroencephalogram signal, and outputs to the output section 6 a function control signal for controlling a function of a device (TV set 11). As a result of this, the output section 6 is able to switch the program to be displayed on the TV screen 12 of the TV set 11 to a program which is desired by the user. In the present specification, a user interface for performing such a manipulation for a device (e.g., the TV set 11) is referred to as an "electroencephalogram interface".

FIG. 4 illustrates an activation apparatus 20 for the electroencephalogram interface system 1. When the electroencephalogram interface system 1 is not functioning, more specifically, when the function control section 5 is not functioning, the activation apparatus 20 causes a visual stimulation to be presented on or vanished from the TV screen 12. Then, based on an event-related potential since the timing of presenting a visual stimulation as a starting point, control as to whether or not to activate the function control section 5 is made.

In the present specification, to begin the operation of a user interface function of the function control section 5 is referred to as "activation of the electroencephalogram interface system". It is supposed that, even if the electroencephalogram measurement section 3 included in the electroencephalogram interface system is operating, "activation of the electroencephalogram interface system" is yet to occur when the function control section 5 is not operating.

Figure 5:
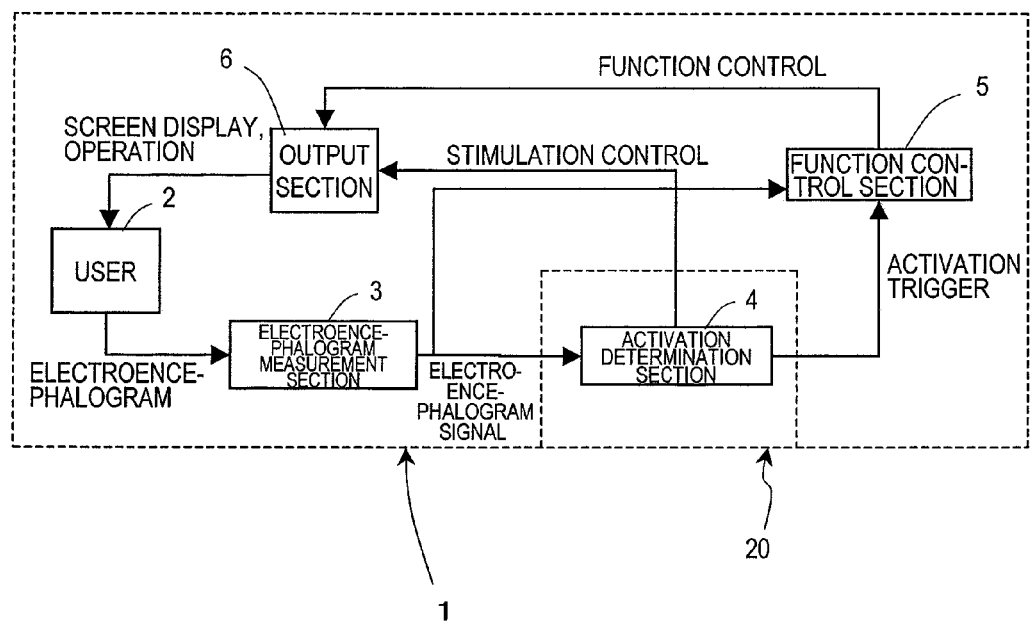
FIG. 5 A diagram showing a functional block construction of the electroencephalogram interface system 1 and an activation apparatus 20.

FIG. 5 shows the functional block construction of the electroencephalogram interface system 1 and the activation apparatus 20. Hereinafter, with reference to FIG. 5, the respective component elements of the electroencephalogram interface system 1 and the activation apparatus 20 will be described.

The electroencephalogram measurement section 3 is an electroencephalograph, for example, and measures an electroencephalogram of the user 2 to output an electroencephalogram signal. When the electroencephalogram interface system 1 is not activated, the measured electroencephalogram signal is sent to the activation apparatus 20. On the other hand, when the electroencephalogram interface system 1 is activated, the measured electroencephalogram signal is sent to the function control section 5.

In response to reception of an activation trigger from the activation apparatus 20, the function control section 5 begins operation. The function control section 5 outputs a function control signal to the output section 6 described later. The function control signal is a signal for controlling a function of a device. For example, based on a function control signal, output control of a menu selection screen of an electroencephalogram interface, menu selection control based on an electroencephalogram, displaying control of TV video, or the like is performed.

The output section 6 outputs a visual stimulation, a menu selection screen, video, or the like for the user 2 onto the TV screen 12.

The activation apparatus 20 includes an activation determination section 4. When the electroencephalogram interface system 1 is not functioning, the activation determination section 4 transmits to the output section 6 a stimulation control signal for controlling the presentation and vanishing of a visual stimulation on a single-item on the output section 6. Moreover, within the electroencephalogram signal acquired from the electroencephalogram measurement section 3, the activation determination section 4 compares the value of the P200 component of an event-related potential since the timing of presenting a visual stimulation as a starting point against a predetermined threshold value. Then, in accordance with the result of comparison, it determines whether or not to output an activation trigger to the function control section 5. When this activation trigger is output to the function control section 5, it becomes possible to activate the electroencephalogram interface system 1.

In the present embodiment, whether or not the user 2 uses an electroencephalogram interface, i.e., whether or not the user 2 allows a user interface function of the function control section 5 to operate, is determined by the activation determination section 4 by utilizing the electroencephalogram of the user 2. The specific operation of the activation determination section 4 will be described later.

As has been generally described, the electroencephalogram interface system 1 is used for providing an interface with which to manipulate the TV set 11 by utilizing an electroencephalogram signal from the user 2. The electroencephalogram signal from the user 2 is acquired by the electroencephalogram measurement section 3 worn on the head of the user 2, and is transmitted to the activation determination section 4 in a wireless or wired manner. The activation apparatus 20 according to the present embodiment, which is internalized in the TV set 11, recognizes a will of activation of the user 2 by utilizing a component which constitutes a part of the electroencephalogram, called an event-related potential, and outputs an activation trigger to the function control section 5.

Upon receiving an activation trigger, the function control section 5 outputs to the output section 6 a function control signal for displaying a menu screen on the TV screen 12. In the present embodiment, the function control section 5 is also internalized in the TV set 11.

Figure 6:
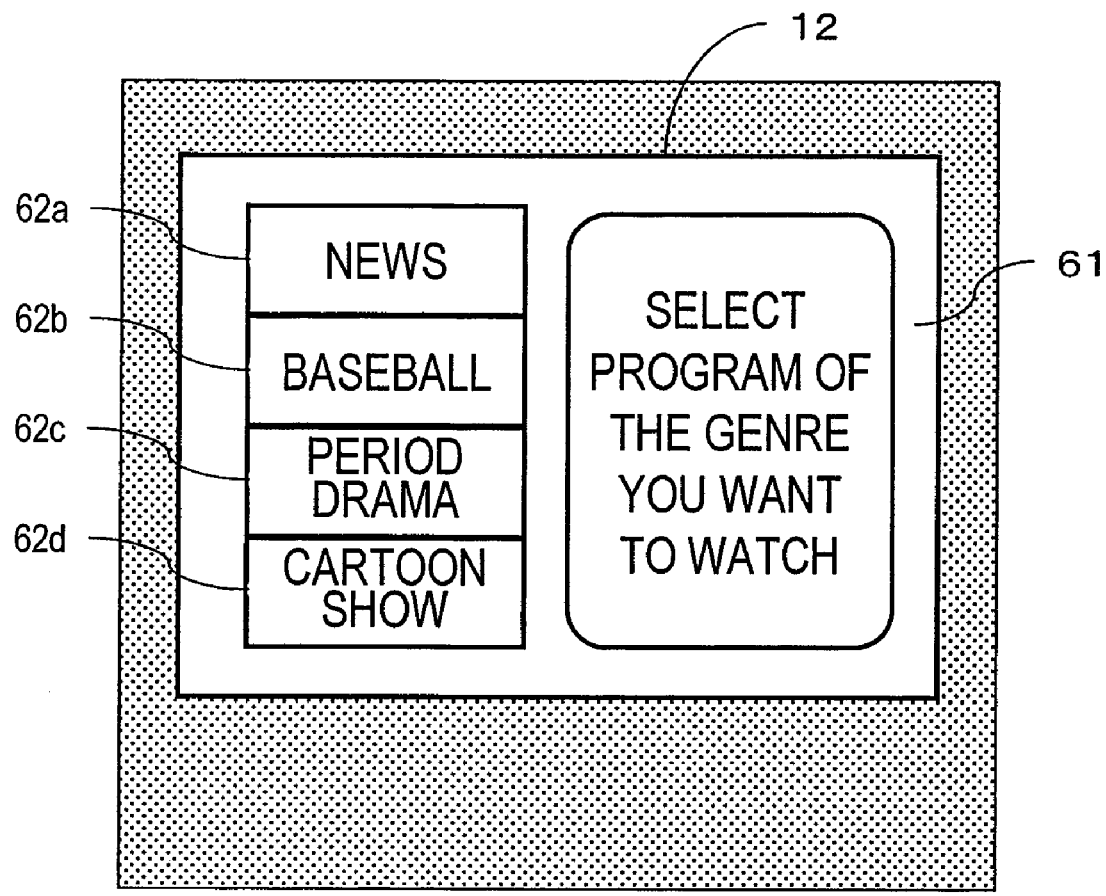
FIG. 6 A diagram showing a menu screen 61 which is displayed on a TV screen 12.

FIG. 6 shows a menu screen 61 which is displayed on the TV screen 12. The device control section 5 recognizes an intent of the user 2 by utilizing a component which constitutes a part of the electroencephalogram, called an event-related potential, selects from among a plurality of selection items displayed on the TV screen 12 a selection item (62a, 62b, 62c, 62d) that is desired by the user 2, and performs a process such as switching of the receiving channel, based on the result of selection. Such a user interface is an "electroencephalogram interface" as referred to in the present specification.

Figure 7:
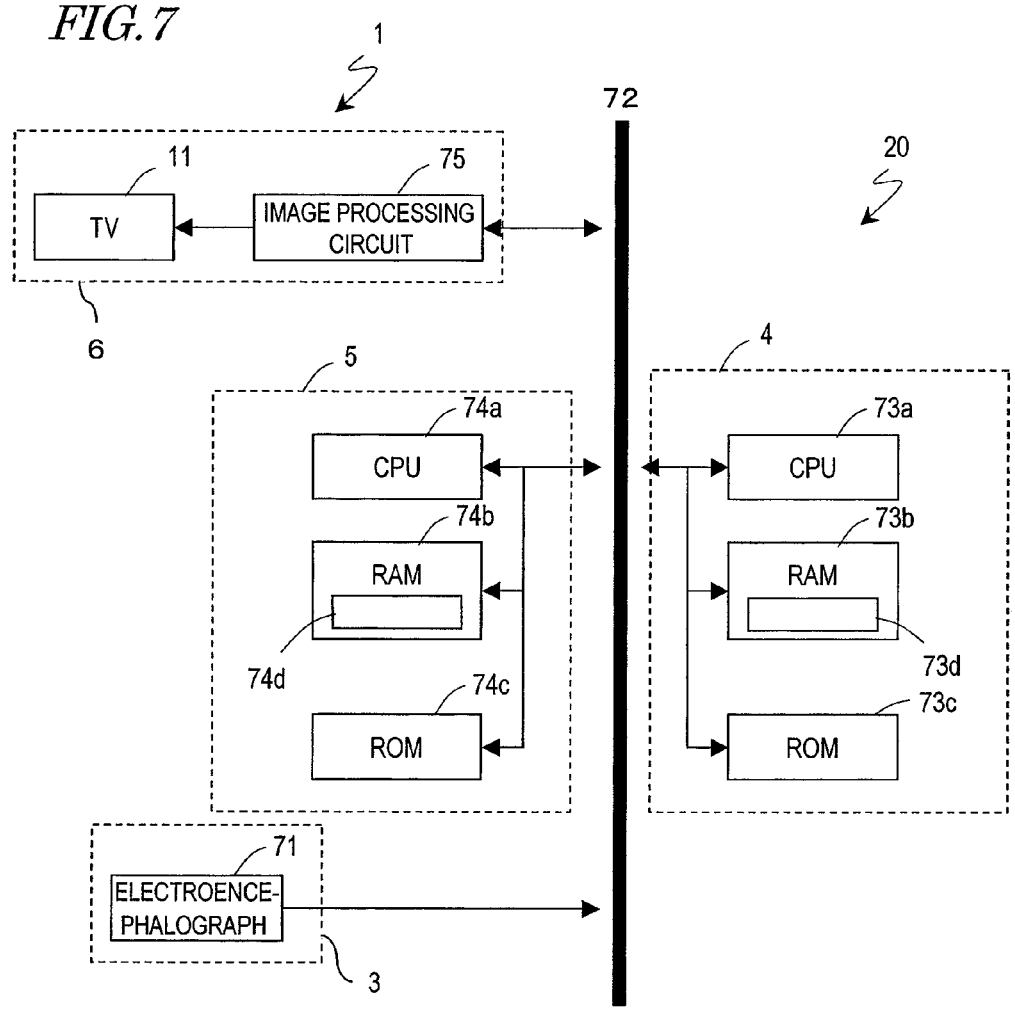
FIG. 7 A diagram showing a hardware construction of the electroencephalogram interface system 1 and the activation apparatus 20 according to Embodiment 1.

FIG. 7 shows the hardware construction of the electroencephalogram interface system 1 and the activation apparatus 20 according to the present embodiment.

The function control section 5, an electroencephalograph 71 which is the electroencephalogram measurement section 3, the output section 6, and the activation determination section 4 of the activation apparatus 20 are connected to a bus 72, so that exchange of signals between the component elements is performed via the bus 72. When the function control section 5 executes an electroencephalogram interface function based on an electroencephalogram signal from the user 2, a consequently-generated instruction signal is sent to the output section 6.

In the present embodiment, the output section 6 includes an image processing circuit 75 and the TV set 11. Based on an instruction signal received from the function control section 5, the image processing circuit 75 performs an image processing, generates a control signal, and sends it to the TV set 11. As a result, the TV set 11 operates.

Note that, although the activation apparatus 20 and the function control section 5 are described as being built in the TV set 11, they do not need to be built in the TV set 11 in terms of their relationship with the electroencephalogram interface function. Therefore, in FIG. 7, the activation determination section 4, the function control section 5, and the TV set 11 are illustrated as independent constituent elements. Moreover, in the case where the electroencephalograph 71 transmits an electroencephalogram signal from the user 2 wirelessly, a wireless transmission section is to be included in the electroencephalograph 71, and a wireless reception section is to be connected to the bus 72.

The activation determination section 4 of the activation apparatus 20 includes a CPU 73a, a RAM 73b, and a ROM 73c. The CPU 73a loads a computer program 73d which is stored in the ROM 73c onto the RAM 73b, and lays it out on the RAM 73b and executes it. In accordance with the computer program 73d, the activation determination section 4 performs a process of determining the necessity to activate a subsequently-described electroencephalogram interface. Note that the ROM 73c may be a rewritable ROM (e.g. EEPROM).

The function control section 5 includes a CPU 74a, a RAM 74b, and a ROM 74c. The respective functions of the CPU 74a, the RAM 74b, and the ROM 74c are similar to those of their namesake component elements in the activation determination section 4. A computer program 74d which is stored on the ROM 74c is intended for processes for realizing an electroencephalogram interface function, whereby the activation determination section 4 and the function control section 5 have different functions. Note that a common CPU, RAM, and ROM may be shared between the activation determination section 4 and the function control section 5, and only separate computer programs may be provided, thus simplifying the construction.

The output section 6 includes an image processing circuit 75. Based on instructions from a CPU 73a and a CPU 74a, the image processing circuit 75 outputs a video signal for causing an electroencephalogram interface activation icon to flicker on the screen of the TV set 11 or to display a menu of an electroencephalogram interface on the screen. Moreover, through control of the function control section 5, the image processing circuit 75 also performs a video outputting process, which is a basic function of a TV set.

The aforementioned computer programs are distributed on the market in the form of products recorded on a storage medium such as a CD-ROM, or transmitted via telecommunication lines such as the Internet. Note that the activation determination section 4 and the function control section 5 can also be implemented in hardware, as computer programs incorporated in semiconductor circuitry, e.g., DSPs.

Figure 8:
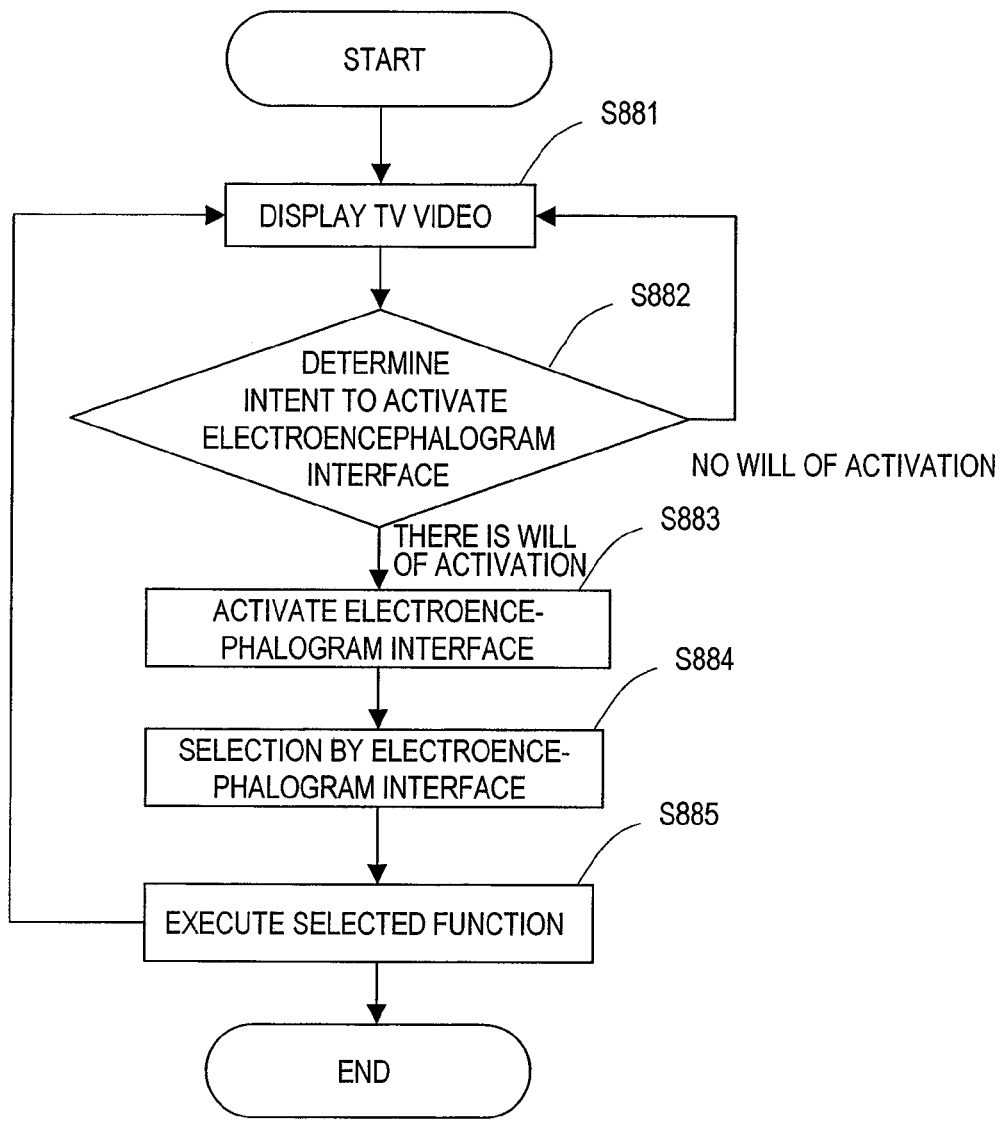
FIG. 8 A flowchart showing the flow of processing by the electroencephalogram interface system 1.

FIG. 8 shows a flow of processing by the electroencephalogram interface system 1. At step S881, TV video is being displayed on the TV screen 12. This is a usual state of the TV set 11.

At step S882, the activation determination section 4 outputs a stimulation control signal to control flickering of the icon 13 which is displayed in a portion of the TV screen 12 as shown in FIG. 1, and based on an electroencephalogram signal which is acquired from the electroencephalogram measurement section 3, determines the user's 2 will of activating an electroencephalogram interface. Specific description of this determination process will be set forth later. If it is determined that the user 2 has no will of activation, the process returns to step S881, and displaying of TV video and flickering of the icon are continued until a will of activation of the user 2 is determined. If it is determined that the user 2 has a will of activation, the process proceeds to step S883.

At step S883, the function control section 5 begins operation, whereby an electroencephalogram interface is activated. Then, at the next step S884, the user 2 utilizes the electroencephalogram interface to select a desired selection item via a menu screen. Through the processing of the electroencephalogram interface at step S883, an option that is desired by the user 2 is chosen. The details of the processing of the electroencephalogram interface will be described later.

At step S885, the function control section 5 executes the selected function. After the function is executed, control returns to step S881 to again display TV video, thus entering a state of awaiting an activation of an electroencephalogram interface. Or, if the selected function is to power Off the TV set 11, the process is ended.

FIGS. 9(a) to (d) show examples where the user 2 watches a program of a genre which he or she wishes to view by manipulating the TV set 11 in the electroencephalogram interface system 1.

Figure 9:
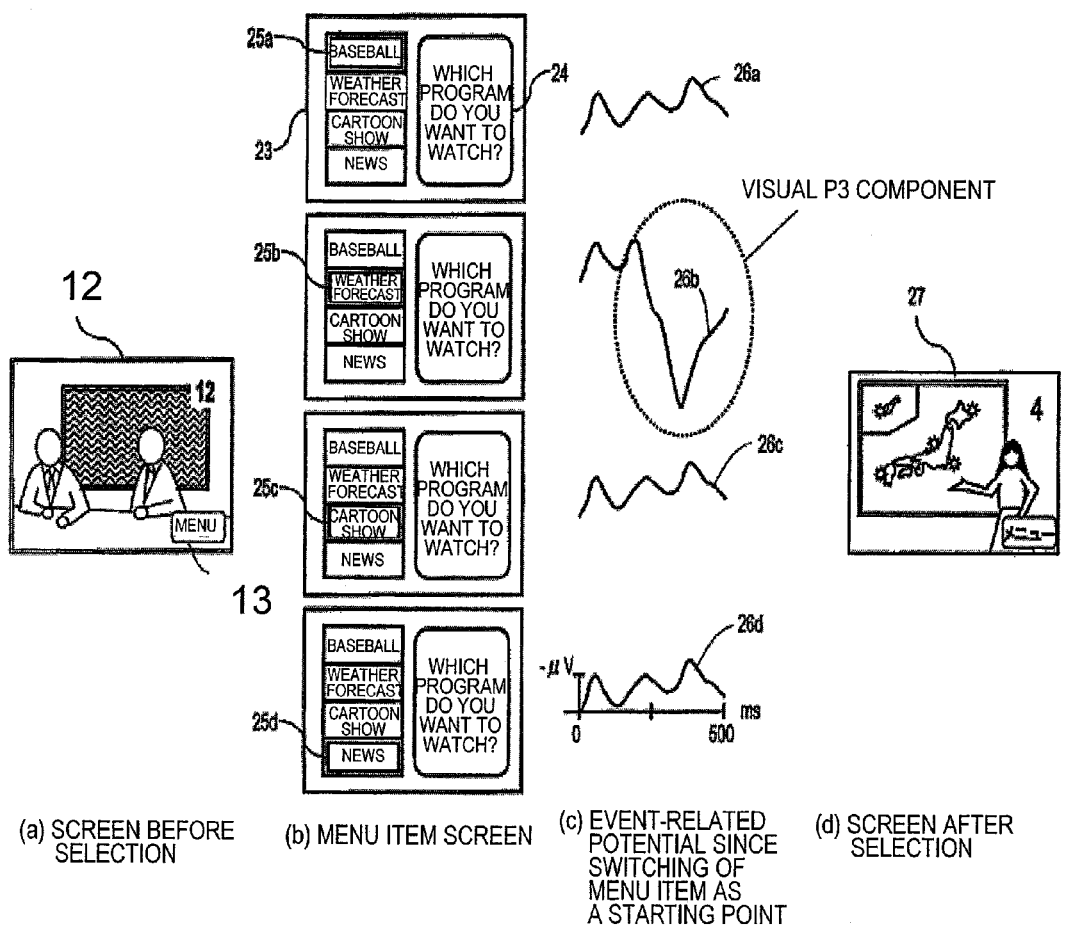
FIG. 9 (a) to (d) are diagrams showing an example where a TV set 11 is manipulated in the electroencephalogram interface system 1 and a user 2 watches a program of a genre which he or she wishes to view.

In FIG. 9(a), an activation icon 13 which flickers with a predetermined frequency is shown on the screen 12. If the activation determination section 4 determines that the user 2 is looking at the activation icon 13, the function control section 5 is activated, whereby the electroencephalogram interface becomes usable. At the same time, a menu item screen of FIG. 9(b) is displayed.

FIG. 9(b) is an example of a menu which the function control section 5 presents to the user 2 via the screen 12 of the TV set. On the screen, a question 24 "Which program do you want to watch?" and options that are candidates of programs whose watching may be desired are displayed. Herein, four options are displayed, i.e., "baseball" 25a, "weather forecast" 25b, "cartoon show" 25c, and "news" 25d.

In the example of FIG. 9(b), baseball 25a which is at the topmost is first selected and receives highlight indication. "Highlight indication" means an indication against a brighter background or indication in a brighter text color than other items, or an indication pointed to by a cursor or the like. Herein, it suffices if it is clear which item the system currently wants attention to, when looked at by the user 2. Next to the fourth "news" 25d, it returns to baseball.

FIG. 9(c) shows event-related potentials of electroencephalogram signals from the user 2 which is acquired by the electroencephalograph 18. The starting point for acquiring an event-related potential is set to a moment when each option is highlight-indicated. An event-related potential from e.g. 200 ms before and until 1 second after this moment is extracted from the electroencephalogram signal. As a result, a response of the user 2 for the item which is highlight-indicated is obtained.

It is assumed that the user 2 is currently wishing to watch "weather forecast" 25b. Among electroencephalogram signals 26a to 26d respectively corresponding to the options 25a to 25d, an electroencephalogram signal 26b from the user when "weather forecast" is highlighted shows that a characteristic positive component (P300 component) appears after a latent period of about 300 ms has lapsed since the point of highlighting "weather forecast" as a starting point. Therefore, determining that the option for which this P300 component has been detected is the program which user 2 wishes to view, the function control section 5 switches the channel to a channel of the weather forecast. FIG. 9(d) shows a screen 27 after the channel of the weather forecast is selected.

Figure 10:
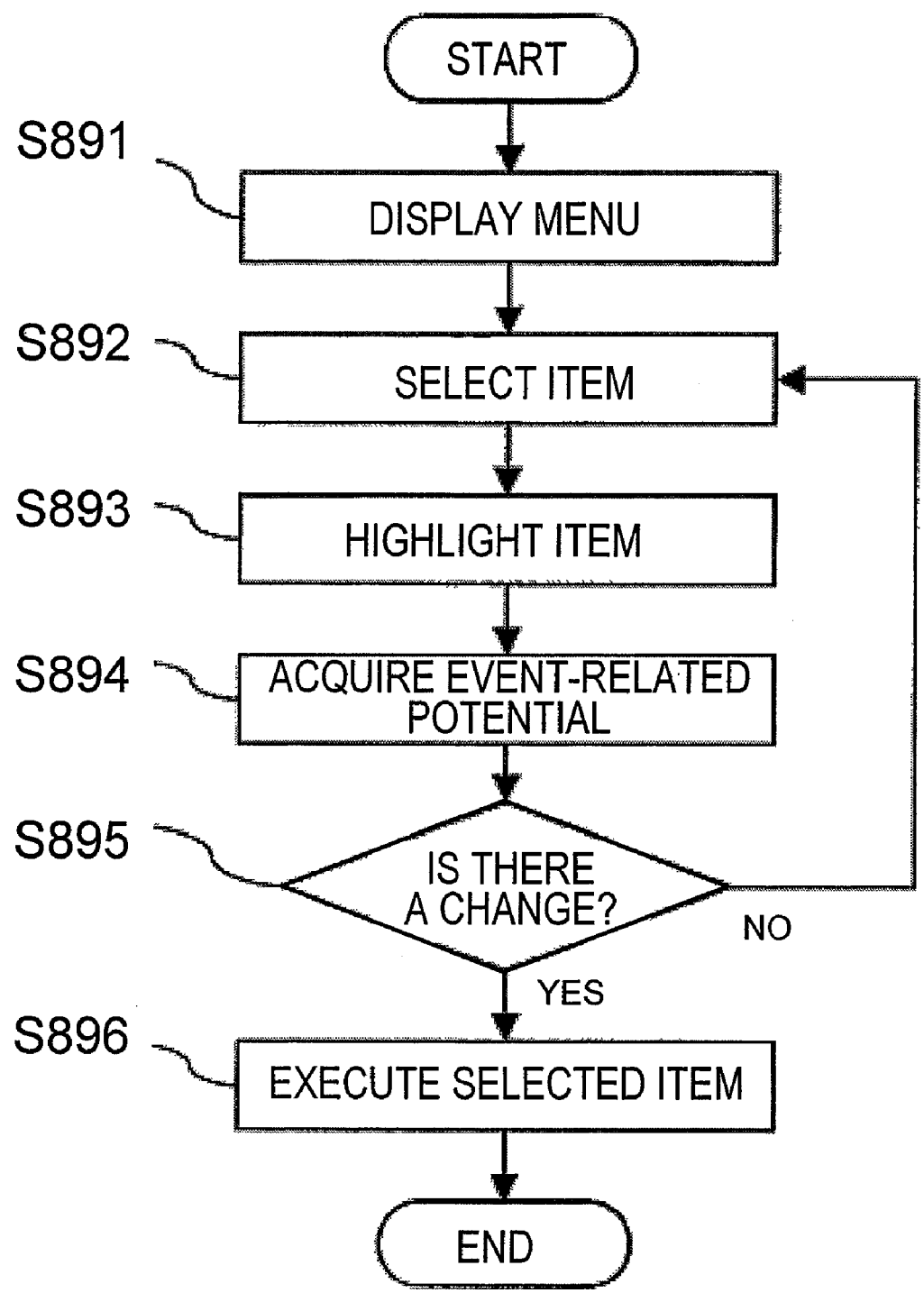
FIG. 10 A flowchart showing a processing procedure by the function control section 5 after activation of an electroencephalogram interface.

FIG. 10 shows a processing procedure by the function control section 5 after activation of the electroencephalogram interface.

At step S891 after activation of the electroencephalogram interface, the function control section 5 displays a menu 23 shown in FIG. 9(b). At step S892, the function control section 5 selects e.g. the item "baseball" 25a, and at the next step S893, highlight-indicates the selected item "baseball" 25a.

At step S894, by using the highlight indication of the item as a starting point, the function control section 5 acquires an event-related potential based on the electroencephalogram signal which is output from the electroencephalogram measurement section 3.

At step S895, the function control section 5 determines whether any waveform change that is associated with highlighting of the item whose selection is desired exists in the acquired event-related potential. If the waveform change exists, control proceeds to step S896; if the waveform change does not exist, control returns to step S892 to perform highlight indication of the next item (e.g. "weather forecast" 25b). By distinguishing the presence or absence of a P300 component, it can be determined whether the waveform of the currently-acquired an electroencephalogram is a waveform for an item which the user 2 wishes to select or a waveform for an item which the user 2 does not wish to select.

At step S896, the function control section 5 executes a function (channel switching) corresponding to the item for which a P300 component has appeared.

Through the above processing, the user 2 can select a menu item based on an electroencephalogram, without manipulating a button. Although it is assumed in step S892 that items are selected in order, a method of randomly presenting them would also be possible. This leads to a possibility that the menu selection might be made more carefully because it is not known in advance which item will be selected.

Figure 11:
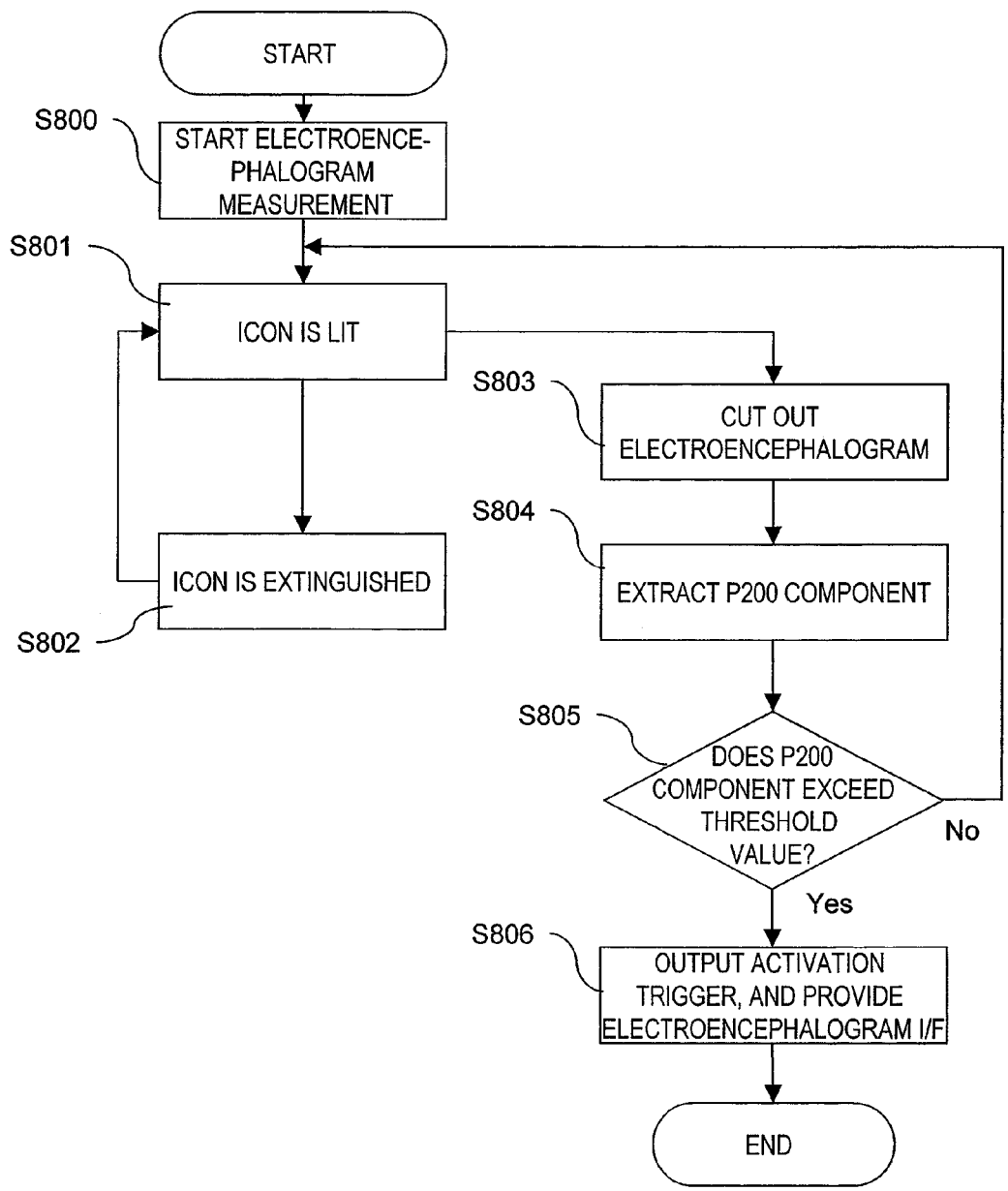
FIG. 11 A flowchart showing a processing procedure related to activation of the electroencephalogram interface according to Embodiment 2.

FIG. 11 shows a processing procedure related to the activation of the electroencephalogram interface according to the present embodiment. The description herein will be given by taking the screen in FIG. 1 as an example. The process shown in FIG. 11 is executed when the user 2 is simply viewing a program on TV while wearing an electroencephalograph, for example.

At step S800, the electroencephalogram measurement section 3 begins measurement from the point of being worn on the head of the user 2. Even while the user 2 is viewing a program on the TV set 11, the electroencephalogram measurement section 3 is always measuring an electroencephalogram signal.

At step S801 and step S802, the activation determination section 4 repeats a process of lighting the icon 13 on the TV screen 12 with a predetermined interval and extinguishing the icon 13 with a predetermined interval, thus causing the icon 13 to flicker.

Concurrently with this operation, at step S803, the activation determination section 4 cuts out the event-related potential in a range containing a P200 component since the timing of lighting the icon 13 as a starting point, from the electroencephalogram signal which is measured by the electroencephalogram measurement section 3. Further at step S804, in a zone of 50 ms before and after about 200 ms since the timing of lighting the icon 13 as a starting point, the activation determination section 4 looks for a positive local maximum value, and extracts the amplitude thereof as a P200 component.

At step S805, the activation determination section 4 determines whether the P200 component exceeds a previously-set threshold value or not. The previously-set threshold value is 4 μV, for example. According to the examples of graphs (a) and (b) in FIG. 3A, by setting 4 μV as the threshold value, it becomes possible to determine the presence or absence of a will of activation based on the P200 component.

At step S805, if the P200 component exceeds the threshold value, the process proceeds to step S806. On the other hand, if the P200 component does not exceed the threshold value, the process returns to step S801, and flickering of the icon 13 is further continued.

At step S806, the activation determination section outputs an activation trigger to the function control section 5, and in response to reception of this activation trigger, the function control section 5 begins to provide an electroencephalogram interface for the user 2.

Thus, by analyzing the electroencephalogram of the user 2 when the icon 13 is lit, it is possible to determine whether it is necessary to activate an electroencephalogram interface or not, and switch the processing of the electroencephalogram interface system 1 based on the determination result.

As described above, by acquiring the electroencephalogram signal from the user, an electroencephalogram interface system is realized which is capable of activating an electroencephalogram interface and selecting a menu item based on an electroencephalogram. A practical electroencephalogram interface system can be provided because the manipulation for a series of processes, consisting of activation and execution of an electroencephalogram interface and processing after switching, are realized based only on an electroencephalogram. Therefore, in situations where both hands are full, e.g., during household chores or while holding a baby, it is possible to activate an electroencephalogram interface and control the operation of a device.

In the above-described example, the P200 component is extracted as the amplitude of a local maximum value in the zone of 50 ms before and after about 200 ms since the timing of lighting the icon 13 as a starting point. However, this is an example. In the case where there are a plurality of positive local maximum values, the maximum value among them may be looked for. Alternatively, instead of a local maximum value, a positive peak (maximum value) in this zone may be looked for. Alternatively, a zone average value in the aforementioned zone may be extracted as the P200 component.

Moreover, although the threshold value against which the value of the P200 component is compared is illustrated as 4 μV, this is also an example. When the output from the electroencephalogram measurement section 3 is being amplified, it may be a value obtained through multiplication by that amplification rate.

The above example is described while assuming that the activation determination section 4 is a functional block for activating the electroencephalogram interface system 1. However, so long as it is in an environment where the user wears an electroencephalograph on the head and thus an electroencephalogram signal can be measured, what is activated may not necessarily be limited to an electroencephalogram interface. For example, powering On/Off of a device and activation of any other interface such as a line-of-sight interface are also encompassed by the activation according to the present invention.

Moreover, although the above example is described while assuming that the output section 6 is a functional block for displaying the activation icon 13, a menu selection screen, and a video content on the TV screen 12, it would also be applicable to separate an output section which is specialized in the displaying of a visual stimulation such as the activation icon 13 from an output section for displaying a menu selection screen and a video content.

Figure 12:
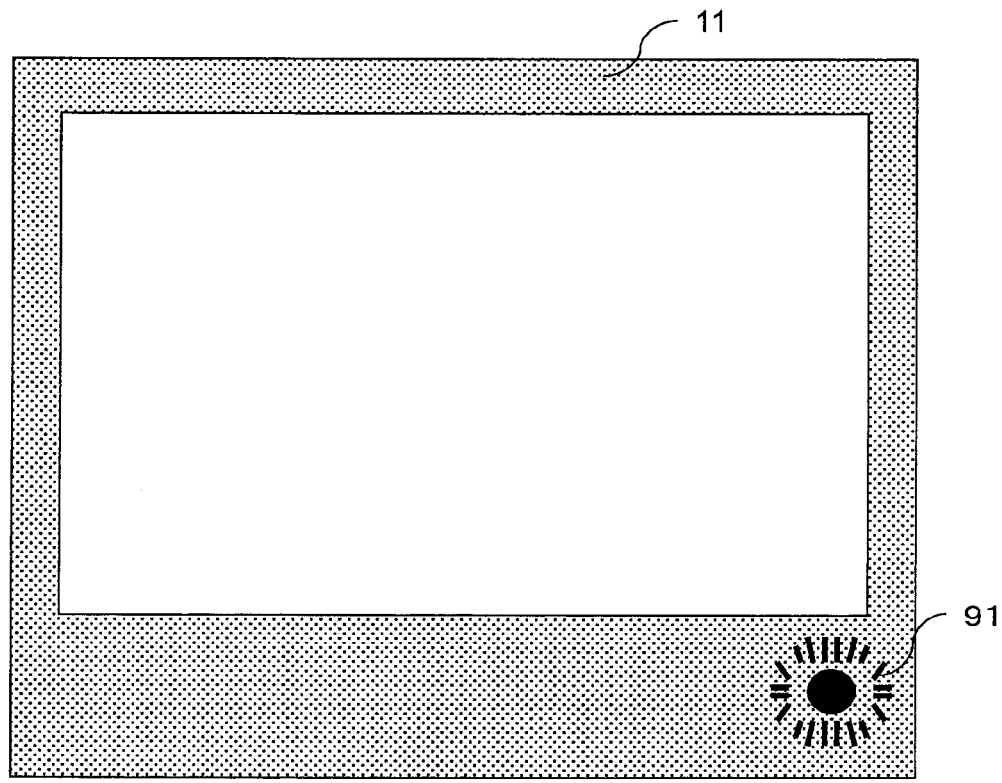
FIG. 12 A diagram showing an example where an LED 91 is provided as a light source for presenting a visual stimulation for activation in a frame portion outside the screen of the TV set 11.

For example, FIG. 12 shows an example where a frame portion outside the screen of the TV set 11, an LED 91 is provided as a light source for presenting a visual stimulation for activation. The LED 91 is also encompassed by the output section 6 as described in the present specification. In the case where the LED 91 is implemented as an independent piece of hardware separate from the TV set 11 at a position away from the screen of the TV set 11 and its frame, the TV set 11 and the LED 91 are encompassed by the output section 6.

Furthermore, the above example is described while assuming that the electroencephalogram interface system 1 is an interface for manipulating the TV set 11. However, what is manipulated may not be a TV set; the present invention is applicable to any apparatus that includes a device which is capable of presenting visual stimulations.

Figure 13:
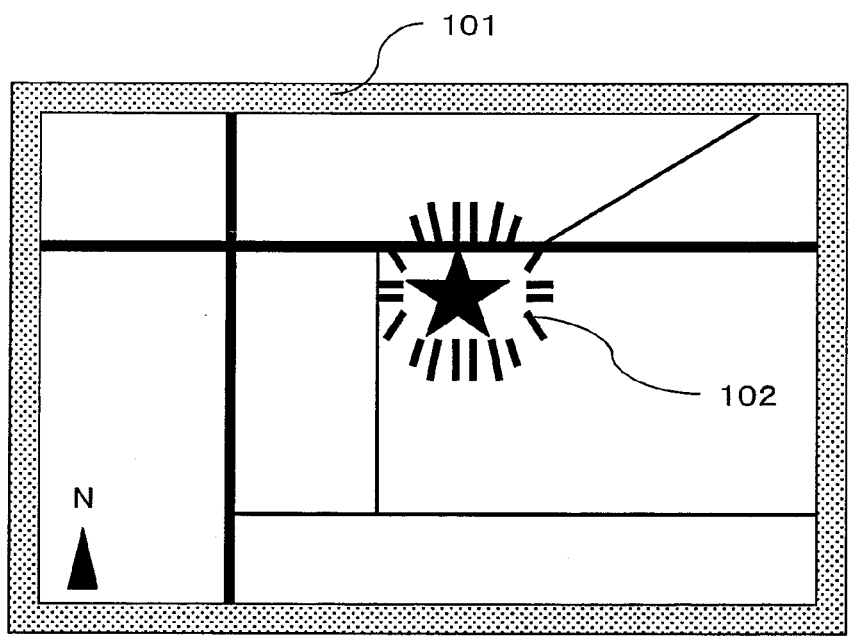
FIG. 13 A diagram showing an example of screen display when manipulating a car navigation system.

For example, FIG. 13 shows an example of screen display when manipulating a car navigation system. Flickering of a map icon 102 on a car navigation screen 101, such as an icon indicating a convenience store or a roadwork, is also considered as flickering of a single item, and the present invention is applicable thereto. An interface which makes a determination of activation in the activation determination section 4, and displays detailed information that is associated with the map icon 102 (an advertisement for that store, information on the engineering work, etc.) is also encompassed by the present invention.

Figure 14:
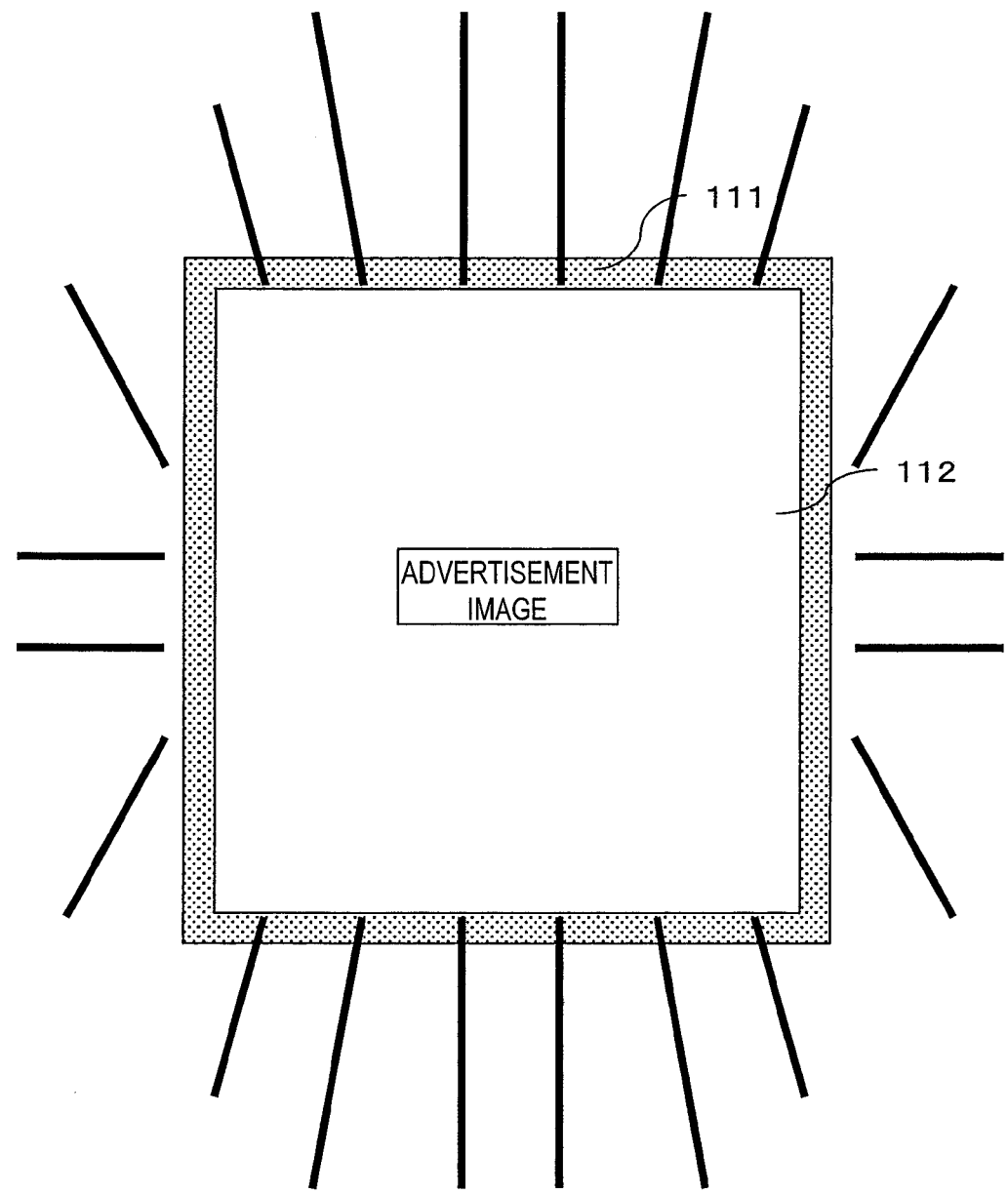
FIG. 14 A diagram showing a flickering advertisement image 112 which is displayed on a screen of a electronic bulletin board system 111.

As still another example, FIG. 14 shows a flickering advertisement image 112 which is displayed on a screen of a electronic bulletin board system 111. The present invention is also applicable to an interface which allows the advertisement image 112 itself to be flickering, and displays detailed information on the product when a determination of activation is made in the activation determination section 4.

Although the present embodiment has been described while assuming that the interval of icon flickering is a constant interval, e.g. 700 ms lit/700 ms extinguished, random intervals or repetitions of lighting/extinction with a shorter period may be used. In these cases, too, the timing of the event-related potential is to be defined since the timing of lighting the icon as a starting point. However, if the lighting timing of the icon is made extremely short, a plurality of positive peaks will occur in the 100 ms zone for detecting the P200 component (a zone of the event-related potential 50 ms before and after about 200 ms), thus making it impossible to extract the P200 component. Therefore, the flickering interval of the icon 13 needs to be controlled so that the icon flickering will occur with a period which is longer than the detection zone (100 ms) for the P200 component.

The above example is described while assuming that, in the activation determination section 4, a determination of occurrence of the P200 component in the event-related potential is made for each lighting of an icon. However, the determination as to whether the P200 component is occurring or not may be made with respect to a waveform which is obtained by taking an arithmetic mean, over a plurality of times of lighting, of the event-related potential during icon lighting. By utilizing a waveform which is obtained by taking an arithmetic mean over a plurality of flickers, the influences of noise components such as blinks are reduced, thus making it possible to reduce the number of incorrect determinations that are made by the activation determination section.

Embodiment 2

In Embodiment 1, every time an icon flickers, the P200 component of the event-related potential is extracted and a determination as to whether there is a will of activation is made. In the present embodiment, in order to further improve the accuracy of the determination of activation, a step of determining whether flickering of the icon is being watched or not on the basis of the event-related potential is provided before operation of the activation determination section 4, and when flickering of an icon is not being looked at, it is excluded from the target of identification for the determination of activation, thus realizing a reduction in device operations that are unintended by the user.

For example, as shown in FIG. 15(a), when it is determined that the user 2 is not watching the icon 13, the icon 13 is undergoing relatively small flickers in an upper left portion of the TV screen 12 of the TV set 11. On the other hand, as shown in FIG. 15(b), when it is determined that the user 2 is watching the icon 13, the icon 13 is displayed in an enlarged size.

In order to describe the principle for realizing the displaying shown in FIGS. 15(a) and (b), the results of the aforementioned experiment are again verified.

In FIG. 3A illustrating the experimental results, three patterns of event-related potentials are shown: solid line (a) representing the case of "paying attention to the icon with a will of activation"; chain line (b) representing the case of "looking at the icon without a will of activation"; and dotted line (c) representing the case of "watching TV video without a will of activation".

It can be seen from FIG. 3A that the state (c) of watching TV video and the state (a) or (b) of looking at the flickering of the icon have greatly different values in a zone of 50 ms before and after about 100 ms since the timing of icon lighting as a starting point. The amplitude value of a negative peak (local minimum value) in this zone is referred to as the "N100 component".

The N100 component is contained in all cases of graphs (a), (b), and (c), and is not considered as occurring due to noise influences. Thus, the inventors have found that, by utilizing this N100 component to previously determine whether the user is watching the icon or not, it is possible to accurately make a determination of activation when the icon is being watched. As a result, a reduction in device operations that are unintended by the user can be realized.

Hereinafter, the construction and operation of an activation apparatus for activating an electroencephalogram interface by utilizing the above-described characteristic features will be described.

Figure 16:
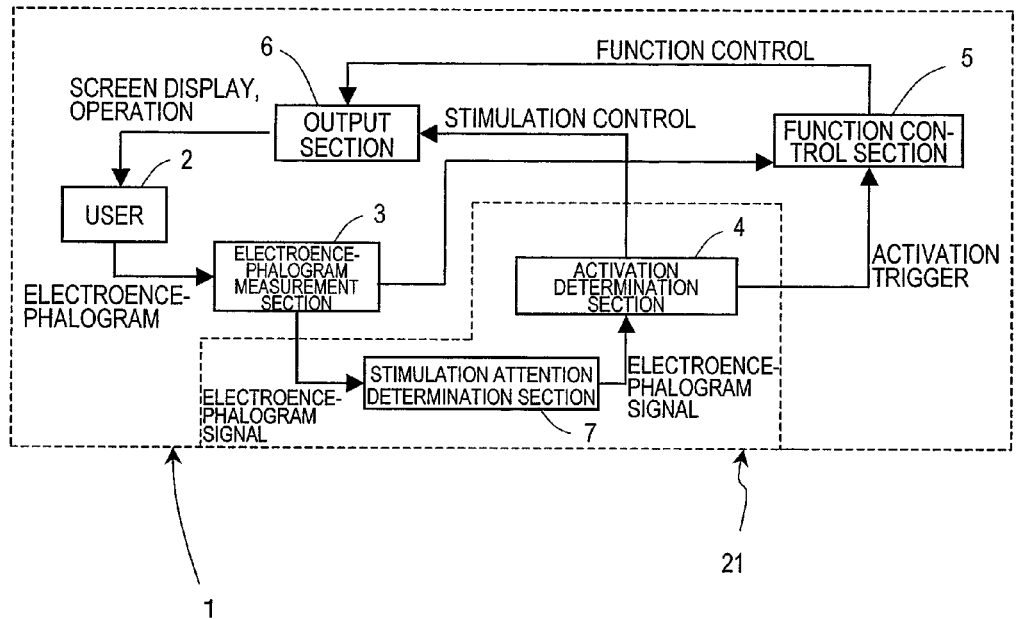
FIG. 16 A diagram showing a functional block construction of an electroencephalogram interface system 11 and an activation apparatus 21 according to Embodiment 3.

FIG. 16 shows the functional block construction of the electroencephalogram interface system 1 and the activation apparatus 21 according to the present embodiment.

In addition to the construction of the activation apparatus 20 of Embodiment 1, the activation apparatus 21 further includes a stimulation attention determination section 7 for determining whether the user 2 is watching the flickering of an icon or not.

Based on the electroencephalogram signal which is measured by the electroencephalogram measurement section 3, the activation apparatus 21 determines whether the user 2 is paying attention to a visual stimulation or not. If it is determined that he or she is paying attention, the electroencephalogram signal measured by the electroencephalogram measurement section 3 is transmitted to the activation determination section 4. Upon receiving the electroencephalogram signal, the activation determination section 4 performs a process of determining a will of activation. Note that, among the component elements of the present embodiment, the component elements which are identical to those of Embodiment 1 (FIG. 5) are denoted by the same reference numerals, and the descriptions thereof are omitted.

Figure 17:
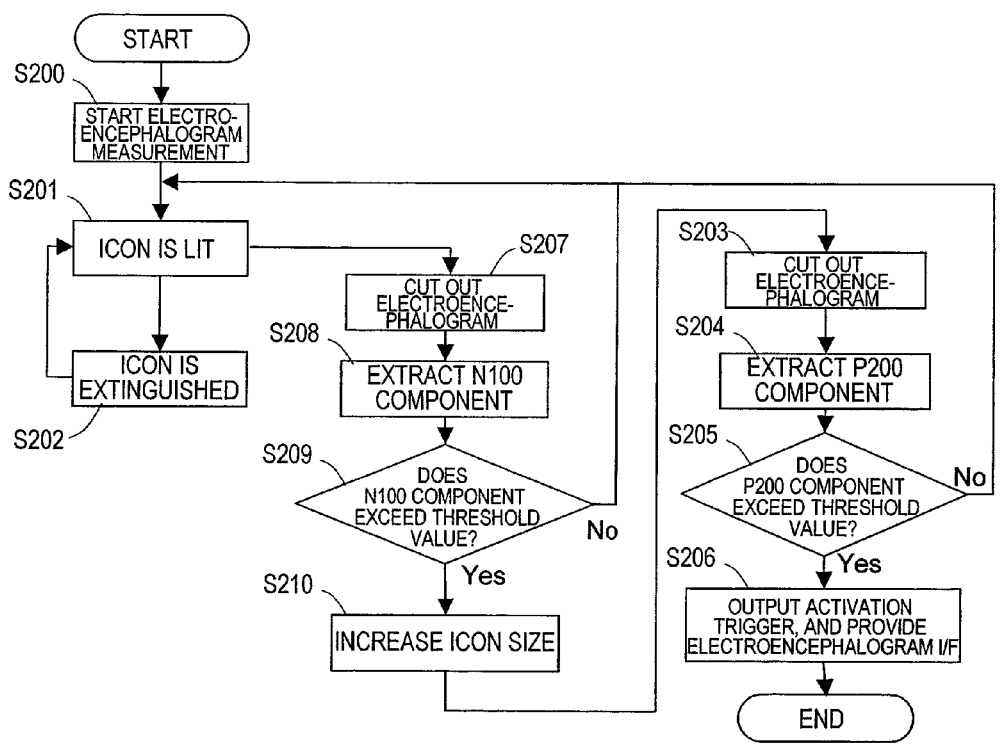
FIG. 17 A flowchart showing a processing procedure related to activation of the electroencephalogram interface according to Embodiment 3.

FIG. 17 shows a processing procedure related to the activation of the electroencephalogram interface according to the present embodiment. It is assumed that, similarly to the process (FIG. 11) of Embodiment 1, the process shown in FIG. 17 is executed while the user 2 is watching TV video, the output section 6 being the TV screen 12.

At step S200, as the user 2 wears the electroencephalogram measurement section 3, the electroencephalogram measurement section 3 begins measurement of an electroencephalogram signal from the user 2. The measurement of the electroencephalogram signal is performed also while the user 2 is watching TV video.

The activation determination section 4 repeats step S201 of lighting the icon 13 on the TV screen 12 with a predetermined interval and step S202 of extinguishing the icon 13 with a predetermined interval, thus flickering the icon 13. As a result, the activation icon 13 keeps flickering in a portion of the TV screen 12, on which TV video is displayed, as shown in FIG. 15(a).

At step S207, the stimulation attention determination section 7 cuts out the event-related potential in a range containing an N100 component since the timing of lighting the icon 13 as a starting point, from the electroencephalogram signal measured by the electroencephalogram measurement section 3.

Further at step S208, in a zone of 50 ms before and after about 100 ms since the timing of lighting the icon 13 as a starting point, the stimulation attention determination section 7 looks for a local minimum value, and extracts the amplitude thereof as an N100 component.

At step S209, the stimulation attention determination section 7 determines whether the N100 component exceeds a previously-set threshold value or not. The previously-set threshold value is −3 μV, for example. In a further generalization, the threshold value is preferably set between the waveforms of the graphs (a) and (b) of FIG. 3A and the waveform of graph (c) (i.e., an intermediate value).

When the N100 component exceeds the threshold value, the process proceeds to step S210. This means that it has been determined that the user 2 is watching the flickering of the icon 13. On the other hand, when the N100 component does not exceed the threshold value, the process returns to step S201. This means that it has been determined that the user 2 is not watching the flickering of the icon 13. Thereafter, the icon 13, which is still being displayed in small size as shown in FIG. 15(a), continues to flicker.

At step S210, the stimulation attention determination section 7 outputs to the activation determination section 4 an instruction signal to increase the displayed size of the icon 13 as shown in FIG. 15(b). The purpose thereof is as follows: when the size of the icon 13 is increased, the icon 13 will naturally come into the field of view and the level of conscious watching can be mildened; and by reducing the influence of TV video on the electroencephalogram, it becomes easier for the P200 component to appear. Upon receiving this instruction signal, the activation determination section 4 outputs to the output section 6 a stimulation control signal for displaying the icon 13 in an enlarged size.

Note that the process of displaying the icon 13 in an enlarged size when the user 2 is watching the flickering of the icon 13 is an example of presenting a visual stimulation with an emphasis.

At the next step S203, based on the stimulation by the icon which is displayed in an enlarged size, the activation determination section 4 cuts out the electroencephalogram. Thereafter, the activation determination section 4 performs an activation determination process from step S204 to step S206. The process of determination of activation is similar to that of Embodiment 1, and the description thereof is omitted.

As described above, in the present embodiment, based on an electroencephalogram signal from the user 2, it is previously determined whether the user 2 is watching the flickering of the icon 13 or not, and if he or she is watching, the icon is increased in size and flickered. As a result, it becomes possible to extract the P200 component based on flickering of a large stimulation. Since the value of the P200 component when the icon is large is greater than the value of the P200 component when it is small, it becomes possible to more clearly determine whether there is a will of activation or not or TV is being watched.

In the above-described example, the N100 component is extracted as the amplitude of a local minimum value in a zone of 50 ms before and after about 100 ms since the timing of lighting the icon 13 as a starting point. However, this is an example. In the case where there are a plurality of local minimum values, the minimum value among them may be looked for. Alternatively, instead of a local minimum value, a negative peak (minimum value) in this zone may be looked for. Alternatively, a zone average value in the aforementioned zone may be extracted as the N100 component.

Embodiment 3

Embodiments 1 and 2 illustrate examples where the flickering of an icon which serves as a stimulation is controlled by the electroencephalogram interface system, and the device to be manipulated is presenting the stimulation via an output section. However, there is a large number of devices to be utilized in our lives, and it would be very difficult to control the flickering of all such devices.

Therefore, in the present embodiment, an activation interface will be described which is applicable even in the case where each device performs flickering with its own timing, rather than the flicker timing being collectively controlled by the electroencephalogram interface system.

In our lives, we encounter various flickering devices, e.g., signboards, neon advertisements, and electronic bulletin board systems. These are flickering with the purpose of catching the eyes of customers, and the final purpose of an advertiser who has installed a signboard or an advertisement is to let customers recognize the details, or let customers buy the product.

However, even if a customer sees a signboard and takes interest in it, over time he or she will often forget the fact that they were once interested, thus not resulting in an eventual buying activity. Moreover, if the advertiser launches an excessive advertisement for customers, those customers who are not particularly interested may be disturbed by the unnecessary information being imposed on them, which might conversely result in a decrease in the customers' buying opportunities.

Therefore, if activities for enhancing the buying desire, e.g., providing discount tickets, can be performed only for those customers who have taken interest in a signboard or advertisement which an advertiser has installed, their buying activities can be effectively promoted. On the part of the customers, too, they become able to obtain only the information concerning the advertisements that they are interested, thus being able to efficiently collect information.

By regarding the aforementioned "customer" as a "user" and the "interest" as a "will of activating a detailed function indication", they are applied to the electroencephalogram interface system and an activation apparatus thereof according to the present invention.

Figure 18:
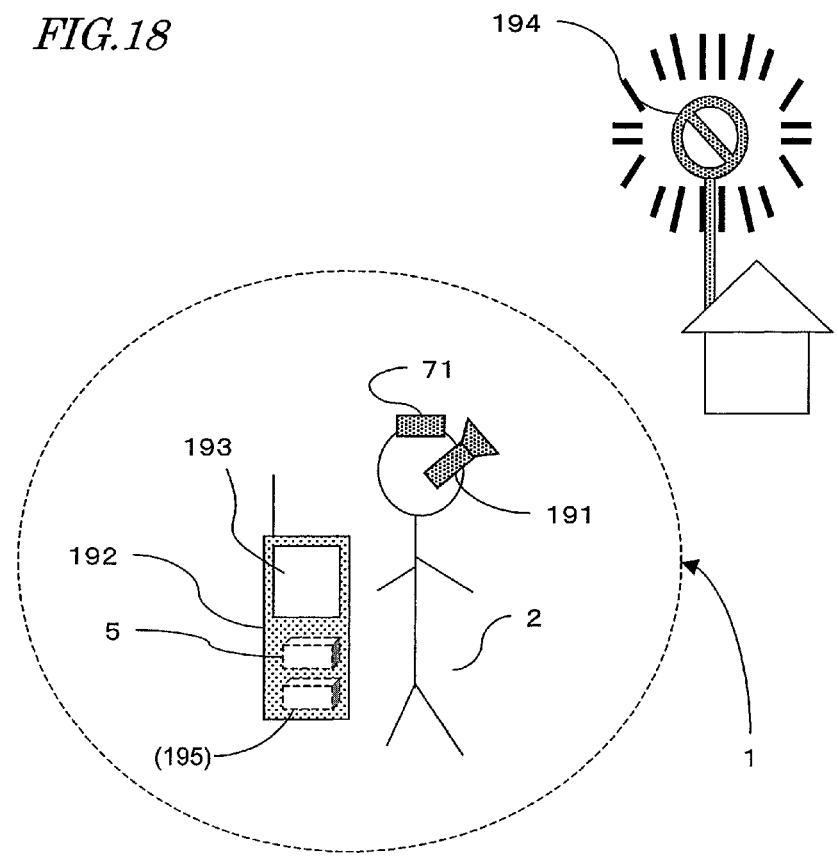
FIG. 18 A diagram showing an environment of use for the electroencephalogram interface system 1 and an activation determination section 4 according to Embodiment 3.

FIG. 18 shows an environment of use for an electroencephalogram interface system 1 and an activation apparatus 195 according to the present embodiment. In the present embodiment, the activation apparatus 195 is incorporated in a mobile phone 192. Note that the activation determination section 4 and the like which have been described in the foregoing embodiments are provided in the activation apparatus 195.

The user 2 is wearing the electroencephalograph 71 and a camera 191 on the head, so that his or her electroencephalogram is always being measured by the electroencephalograph 71. The camera 191 is provided in order to detect a flickering object (e.g., a signboard 194) which has entered into the field of view of the user 2, and is aimed toward the front of the user 2.

The electroencephalogram interface system 1 and the activation apparatus 195 as such are utilized in the following situation. For example, while walking in town, among flickering advertisements, the user 2 may see an advertisement for which he or she desires detailed information; then, the user 2 will watch the flickering of the advertisement with a will of activation.

If the activation apparatus 195 determines a will of activation of the user 2, a previously-set function is activated in the mobile phone 192 that the user 2 is carrying.

For example, a restaurant's signboard 194 may be flickering, and the user 2 may watch the flickering of the signboard 194 with a will of activating a detailed information indication. Then, the activation apparatus 195 determines the will of activation of the user 2, and displays a discount coupon for the restaurant on a display 193 of the mobile phone 192, which is an output section of the electroencephalogram interface system.

Figure 19:
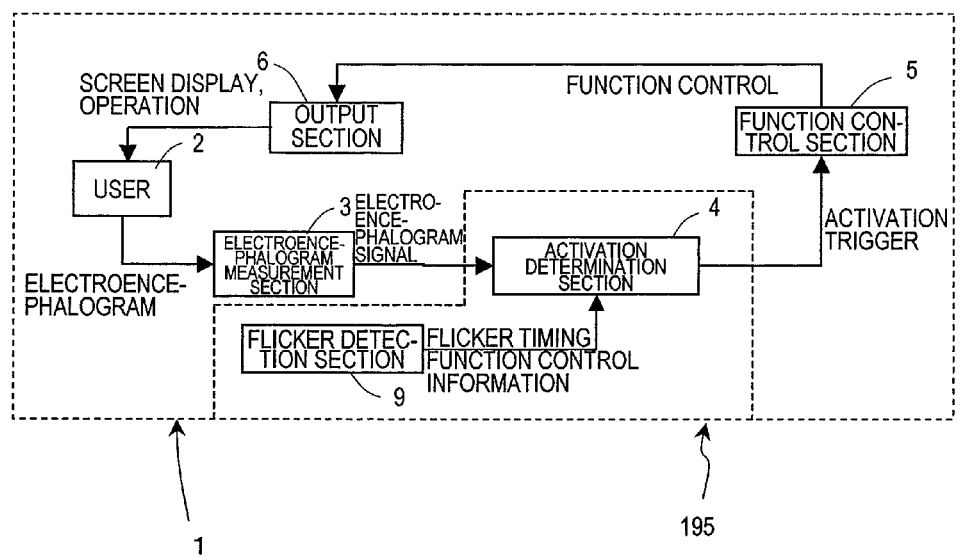
FIG. 19 A diagram showing a functional block construction of the electroencephalogram interface system 1 and an activation apparatus 195 according to Embodiment 3.

FIG. 19 shows the functional block construction of the electroencephalogram interface system 11 and the activation apparatus 195 of the present embodiment. In addition to the construction of the activation apparatus 20 of Embodiment 1, a flicker detection section 9 is further included. The flicker detection section 9 determines the flicker timing of an external flickering object and determines a function to be executed upon determination of activation. Then, to the activation determination section 4, the flicker detection section 9 outputs information indicating the flicker timing and function control information identifying the function which is to be executed upon determination of activation.

The activation determination section 4 identifies the timing of presenting the visual stimulation based on the information indicating flicker timing, performs the processing described in Embodiment 1, and determines whether or not to output an activation trigger. In the case of outputting an activation trigger, it also outputs a control signal for causing a function corresponding to the function control information received from the flicker detection section 9 to be executed.

Figures 20, 21:
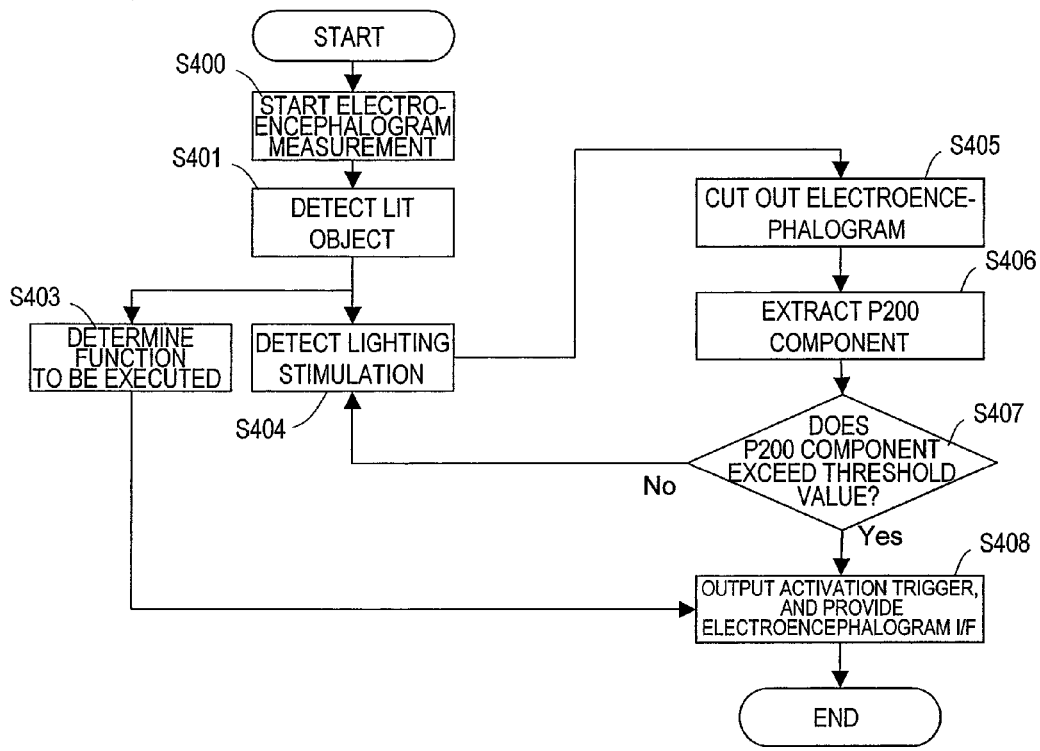
FIG. 20 A flowchart showing a processing procedure related to the activation of an electroencephalogram interface according to Embodiment 3.
FIG. 21 A diagram showing an exemplary database defining correspondence between shop/object information and operating functions.

FIG. 20 shows a processing procedure related to activation of the electroencephalogram interface of the present embodiment.

At step S400, the user 2 wears the electroencephalogram measurement section 3, whereby the electroencephalogram measurement section 3 begins measurement of an electroencephalogram signal from the user 2.

At step S401, based on the video of the camera which is aimed toward the front of the user 2, the flicker detection section 9 searches for any flickering object in the field of view, and detects its presence.

At the subsequent step S403, the flicker detection section 9 determines a function to be executed when a will of activation is detected. Specifically, with the camera 191, the flicker detection section 9 images a flickering signboard or logo mark, etc., of a convenience store, performs a pattern recognition through image processing, and/or acquires object information by utilizing an RF tag, thus identifying a flickering object. Then, the flicker detection section 9 determines the function to be executed based on a prestored database defining the correspondence between the shop/object information and operating functions.

FIG. 21 shows an exemplary database. It is described how to utilize the database in connection with step S403. For example, when the line of sight is directed in the direction of the signboard 194 shown in FIG. 18, the camera 191 which is worn in the line of sight direction images a video of the signboard 194, and outputs a video signal. The flicker detection section 9 acquires the output video signal, detects a flickering subject in the imaged video, i.e., the signboard 194, and performs a pattern recognition for the image.

The flicker detection section 9 refers to the database of FIG. 21 based on the result of pattern recognition for the image, and from the reference result, determines that the flickering signboard 194 belongs to "Delicious Restaurant", and sets the function to be executed upon determining a will of activation of the user 2 to "display a discount coupon".

FIG. 20 is again referred to. Concurrently with step SS403, the flicker detection section 9 performs the process of step S404. The processing after step S404 is an activation determination process utilizing an electroencephalogram signal from the user 2.

At step S404, the flicker detection section 9 detects the timing at which the flickering object was lit, and sends the substance of the function to be executed and the lighting timing to the activation determination section 4.

Steps S405, S406, and S407 are identical to steps S803 to S806 in FIG. 11, and the activation determination section 4 makes a determination of a will of activation by utilizing the P200 component.

If the P200 component does not exceed the threshold value, control returns to the lighting stimulation detection of step S404, and the process is repeated. Conversely, if the P200 component exceeds the threshold value, at step S408, in accordance with the function to be executed as determined by the flicker detection section 9, the activation determination section 4 outputs to the function control section 5 an activation trigger for the function to be executed. As a result of this, it becomes possible to determine a will of activation even with respect to a device whose flicker timing is not controlled by the electroencephalogram interface system 1.

Embodiment 4

Embodiment 1 describes a method which flickers one icon to activate one function of a TV set (electroencephalogram interface), and makes a determination of activation by utilizing the P200 component of an event-related potential when the icon is lit.

In our life environment, numerous devices and functions exist other than TV sets. In order to realize activation of these devices and functions by utilizing the present invention, it does not suffice to activate one function with the flickering of one icon.

Moreover, by consecutively flickering icons that belong to the respective devices, it will be possible to select a device which a user wishes to use, by utilizing the P300 component of the event-related potential. When the number of devices to choose from is as many as ten and a few, or several dozens, a very long time will be required by consecutively lighting the icons of such devices, thus making it difficult to select a device to use with the timing as desired by the user.

Therefore, the present embodiment realizes an activation interface which causes the respective icons of devices to flicker with a plurality of timings, and determines which icon the user has watched with a will of activation. Such an activation interface can be considered as a process in which a determination of a will of activation based on a single type of visual stimulation is performed at a plurality of timings, and therefore the subject matter of the present invention is applicable thereto.

Instead of activation of an electroencephalogram interface which is aimed at a TV set, the present embodiment is directed to a manipulation interface of devices such as a microwave oven and an electromagnetic cooker. Specifically, an activation interface which turns On/Off the power of devices by utilizing flickering of the LEDs of devices will be described.

Note that there is a similarity to Embodiment 1 in that devices are controlled by using an electroencephalogram. Therefore, in the present embodiment, too, the entire system including such an activation apparatus will be referred to as an "electroencephalogram interface system".

Figure 22:
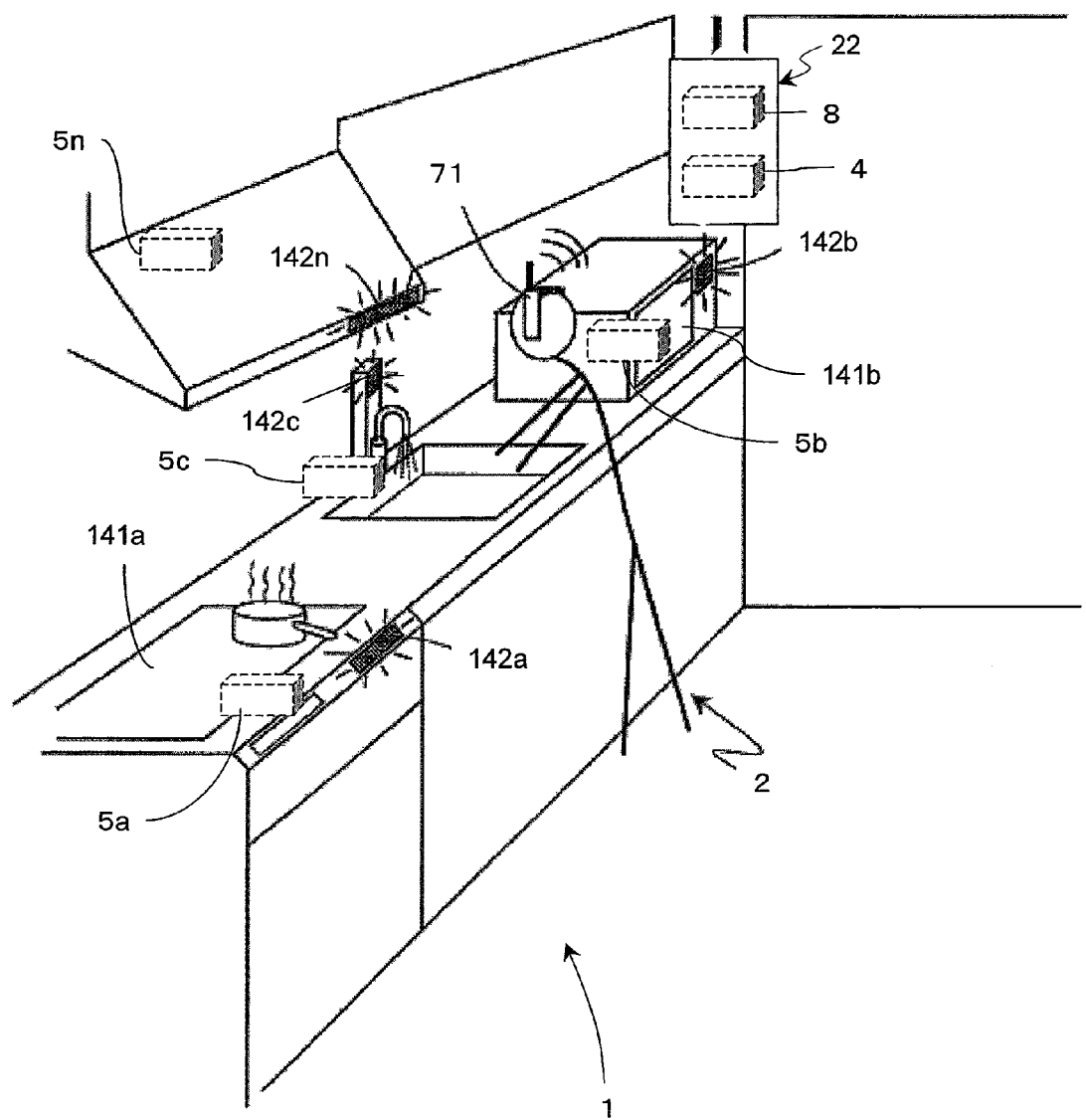
FIG. 22 A diagram illustrating an environment of use for the electroencephalogram interface system 1 and an activation apparatus 22 according to Embodiment 4.

FIG. 22 shows an environment of use for an electroencephalogram interface system 1 and an activation apparatus 22 according to the present embodiment. The electroencephalogram interface system 1 and the activation apparatus 22 are used in a situation where household chores are performed in a kitchen.

In a kitchen, many tasks exist which involve the use of both hands, e.g., washing and cooking, and during such tasks, the user 2 cannot perform any other tasks. On the other hand, the user 2 needs to simultaneously handle many devices and cooking utensils.

The inventors have paid attention to the fact that simple control is requested for many of the devices and cooking utensils that are handled, thus realizing activation of a device and stopping of its operation by using the activation apparatus 22. As a result, even during a task which occupies both hands of the user 2, it becomes possible to activate various kinds of devices and stop their operations.

The user 2 is wearing an electroencephalograph 71. The activation apparatus 22 includes an activation determination section 4 and a flicker timing control section 8. The activation apparatus 22 wirelessly detects an electroencephalogram signal from the user 3 which is detected by the electroencephalograph 71.

Each device such as an electromagnetic cooker 141a or a microwave oven 141b installed in a kitchen has a stimulation presentation section (61a, 61b) such as an LED and a function control section 5, and is flickering with a different timing. The flicker timing is managed by the flicker timing control section 8 in terms of a flicker start time and a flickering period, being controlled so that the flicker timings of the respective device do not coincide. Moreover, the activation apparatus 22 wirelessly controls the flicker timings of LEDs (142a, 142b, 142c, . . . , 142n), and outputs an activation trigger to a function control section (5a, 5b, 5c, . . . , 5n) of each device.

The user 2 watches the flickering of the LED belonging to a device which he or she wishes to control. If the user 2 watches it with a will of activation, the P200 component of an event-related potential since the timing of lighting the LED as a starting point takes a relatively high value. As the user 2 continues to watch with a will of activation, the P200 component will keep appearing in accordance with the flicker timing of the LED. Therefore, by comparing this flicker timing of the LED and the timing of the P200 component occurrence, it becomes possible to identify which device's LED the user 2 has been watching. At this time, in order to exert a predetermined control over each device, the activation apparatus 22 transmits an activation trigger to the function control section 5 of the selected device.

Figure 23:
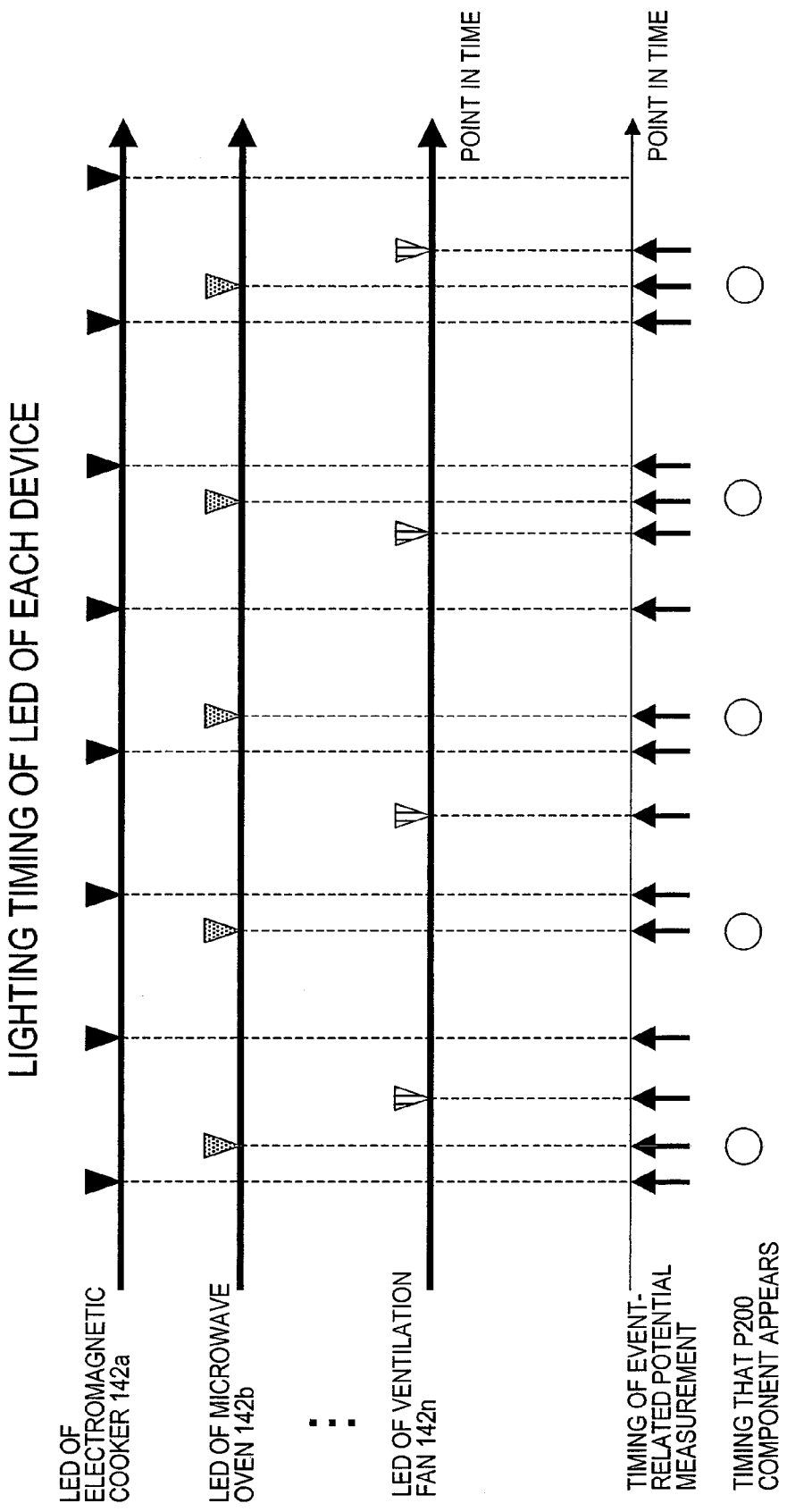
FIG. 23 A diagram showing a relationship between lighting timings of LEDs 142a to 142n of respective devices.
Figures 24, 25:
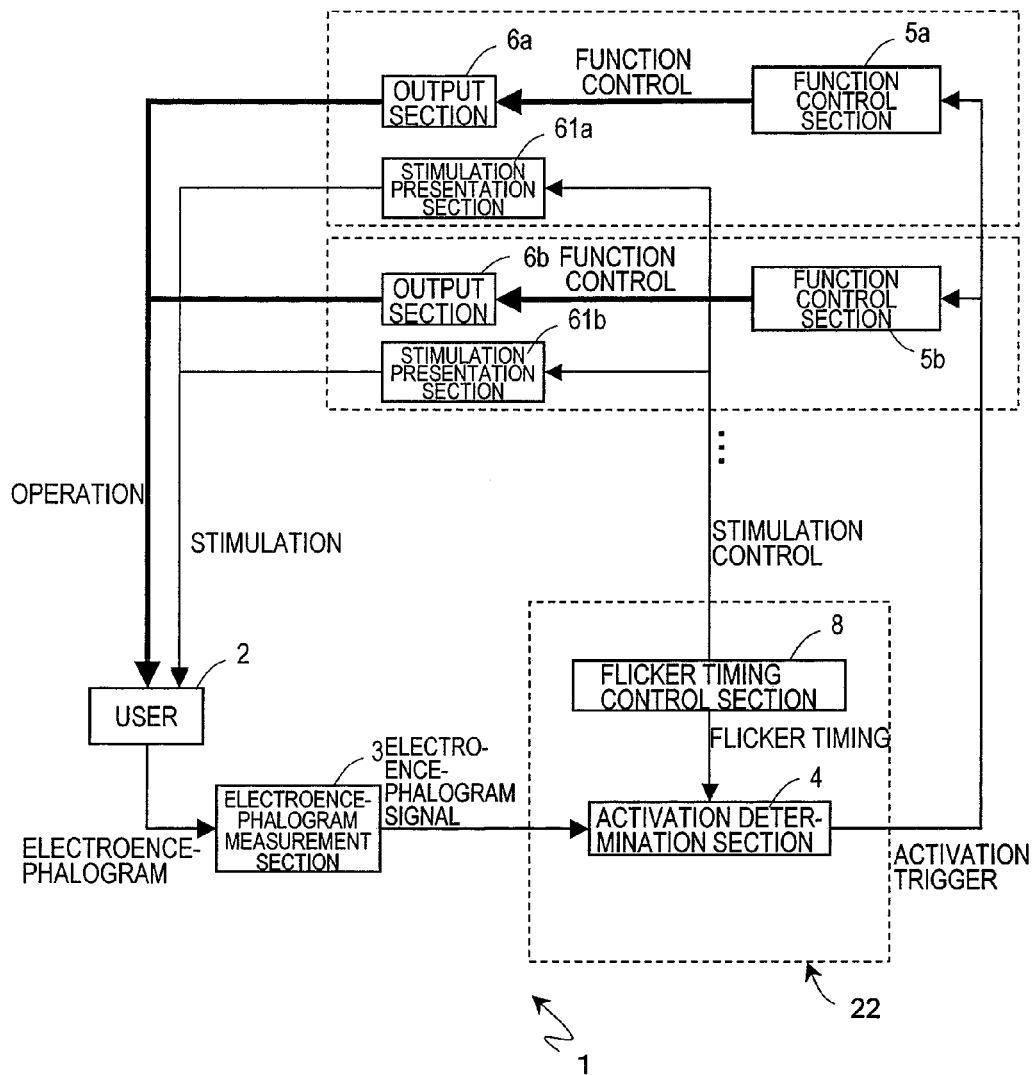
FIG. 24 A diagram showing an exemplary correspondence between the device name of each device shown in FIG. 22, a lighting timing for a flicker device which is provided for each device, and a corresponding device operation.
FIG. 25 A diagram showing a functional block construction of the electroencephalogram interface system 1 and the activation apparatus 22 according to Embodiment 4.

FIG. 23 shows a relationship between the lighting timings of the LEDs 142a to 142n of the respective devices. Each device repeats lighting with a predetermined lighting timing. FIG. 24 shows an exemplary correspondence between the device name of each device shown in FIG. 22, a lighting timing for a flicker device which is provided for each device, and a corresponding device operation. Based on this correspondence, detection of the timing of the P200 component occurrence is performed, and the device operation is determined.

Referring back to FIG. 23, a method of comparison between the flicker timing and the timing of the P200 component occurrence will be described. The flicker timing control section 8 controls the lighting start time and flickering period of the LED of each device, and also performs management so that the lighting points of the LEDs of the respective devices do not coincide. The flicker timing control section 8 predicts the flicker timing of each device from the lighting start time and flickering period.

If the prediction result indicates that the lighting timings of the LEDs of some devices coincide, the lighting timing of one of the LEDs is shifted to a point in time which does not coincide with the lighting point of the LED of the other device. For example, the flicker timing control section 8 delays by 100 ms the lighting point of the LED of the device whose device No. (which is previously assigned to each device) is larger. As a result, the flicker timings are controlled so as not to coincide.

Moreover, if there is a coinciding detection zone for the P200 component at the flicker timings of the LEDs of a plurality of devices, it may not be possible to determine which device's LED a positive peak that has occurred in the coinciding zone has responded to as a P200 component. Therefore, the flicker timing control section 8 performs an adjustment so that the detection zones for the P200 component at the respective flicker timings do not coincide (i.e., so that the flicker timing of the LED of each device is not equal to or less than 100 ms). When a coincidence is predictable from the lighting start times and flickering periods, the flicker timing control section 8 modifies the lighting timing of LED of one device to a timing which is delayed by 100 ms or more from the lighting timing of the LED of the other device.

Under the control of the flicker timing control section 8, each device (141a, 141b, 141c, . . . , 141n) flickers the LED (142a, 142b, 142c, . . . , 142n) which is the stimulation presentation section 61 that the device has. At the lighting timings of all devices, the activation determination section 4 takes event-related potential measurements, detects any event-related potential that has the P200 component among the measured event-related potentials, and determines the occurrence timing of that P200 component. Moreover, the activation determination section 4 compares the timing of the P200 component occurrence and the lighting timing of the LED of each device, and searches for a matching timing, thus identifying which device a will of activation is being possessed for.

FIG. 25 shows the functional block construction of the electroencephalogram interface system 1 and the activation apparatus 22 according to the present embodiment. The construction according to the present embodiment is based on the construction of Embodiment 1, with the flicker timing control section 8 being newly provided in the activation apparatus and the stimulation presentation sections 61a, 61b . . . being provided in the electroencephalogram interface system 1.

For example, the device in the uppermost layer of FIG. 25 includes the stimulation presentation section 61a, the output section 6a, and the function control section 5a. The stimulation presentation section 61a presents a stimulation by utilizing an LED or the like. The output section 6a gives out a function of the device to the user 2. The function control section 5a executes a function which is previously set for that device.

The other devices in the electroencephalogram interface system 1 are similarly constructed.

The flicker timing control section 8 of the activation apparatus 22 collectively controls the timing of lighting/vanishing in the stimulation presentation section 61 possessed by each device.

Figure 26:
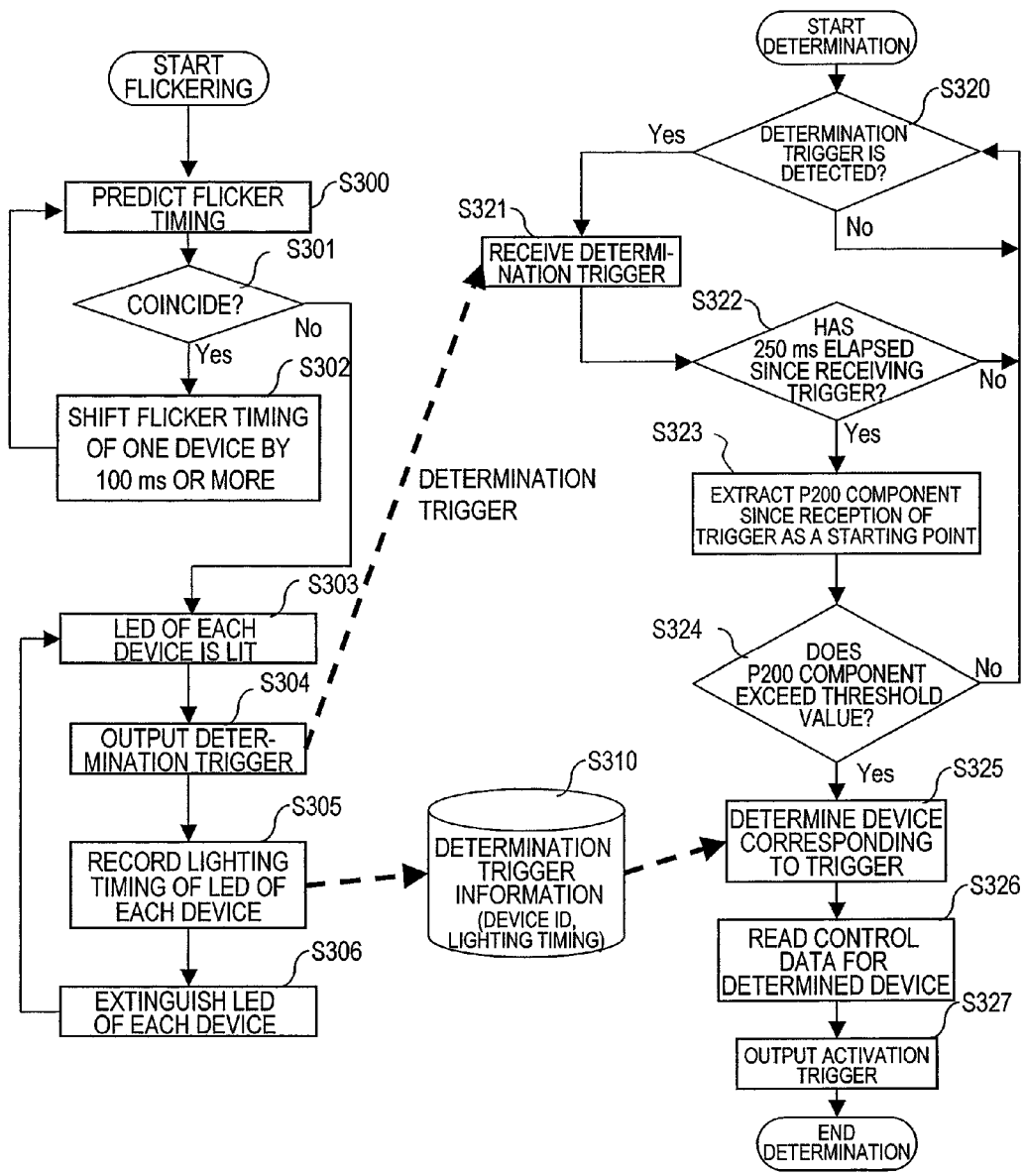
FIG. 26 A flowchart showing a processing procedure related to the activation of an electroencephalogram interface according to Embodiment 4.

FIG. 26 shows a processing procedure related to the activation of an electroencephalogram interface according to the present embodiment.

In FIG. 26, the mainly the processes on the left-hand side are executed by the flicker timing control section 8, and the processes on the right-hand side are executed by the activation determination section 4.

At step S300, the flicker timing control section 8 predicts the lighting timing of each device based on the lighting start time and the lighting period of each device shown in FIG. 24. Then, at step S301, the flicker timing control section 8 determines whether or not there exists any point in time that such lighting timings coincide. If a coinciding point in time exists, the process proceeds to step S302; if no such point in time exists, the process proceeds to step S303.

At step S302, the flicker timing control section 8 shifts the flicker timing of one of the devices by 100 ms or more. As a result, coincidence is eliminated for this point in time that the lighting timings coincide. However, by shifting the lighting timing, a coincidence may possibly occur with the lighting timing of some other device. Therefore, the process again returns to step S300, and the flicker timing control section 8 repeats the processes from step S300 to step S302 until there is no coincidence.

At step S303, the flicker timing control section 8 sends a control signal to each device, and lights the LED of each device. Through the processes from steps S300 to S302 above, it is always the LED of a single device that is lit.

At step S304, when the LED of any device is lit, the flicker timing control section 8 outputs a determination trigger to the activation determination section 4. This determination trigger is used in the activation determination section 4, described later, to determine a zero time reference for extraction of the P200 component of the event-related potential.

At step S305, the flicker timing control section 8 records the lighting timing of the LED of each device to a storage medium (not shown). As a result, as shown in step S310, determination trigger information is accumulated in the storage medium. The determination trigger information describes, for example, a device ID for identifying the device, the lighting timing of that device, and the like. "The lighting timing of the device" may be a point in time at which the device was actually lit, or a difference from a previous lighting timing.

At step S306, the flicker timing control section 8 extinguishes the LED of each device.

The processes from step S303 to S306 are processes since a given device is lit until it is extinguished. These processes are performed for each lighting of a device as shown in FIG. 23.

Next, the processes of steps S320 and later will be described.

At step S320, the activation determination section 4 is awaiting the detection of a determination trigger. Upon detecting a determination trigger, at step S321, the activation determination section 4 receives the determination trigger.

At the next step S322, the activation determination section 4 withholds its processing until 250 ms elapses after receiving the determination trigger. The reason is that, in order to extract the P200 component, an electroencephalogram signal from 150 ms to 250 ms after lighting of the LED (i.e., after reception of the determination trigger) is necessary. If such has elapsed, the process proceeds to step S323; if it has not, the process returns to step S320.

At step S323, from the electroencephalogram signal from the electroencephalogram measurement section 3, the activation determination section 4 cuts out the event-related potential in a range containing a P200 component since the point in time of receiving the determination trigger as a starting point. Then, in a zone of 50 ms before and after about 200 ms since this zero time reference, the activation determination section 4 looks for a positive local maximum value, and extracts the amplitude thereof as a P200 component.

At step S324, the activation determination section 4 determines whether the P200 component exceeds a previously-set threshold value or not. In the case of exceeding, the process proceeds to step S325; in the case of not exceeding, the process returns to step S320.

At step S325, based on the determination trigger information accumulated at step S310, the activation determination section 4 determines a device which was being lit when that determination trigger was output. For example, if the outputting of a determination trigger from the flicker timing control section 8 and the reception of the determination trigger by the activation determination section 4 are to occur substantially simultaneously, the activation determination section 4 searches through the determination trigger information by using the point in time of receiving the determination trigger as a key, and identifies a device which was being lit at that point in time.

At step S326, the activation determination section reads the control data of the determined device from a memory (not shown). As a result, at step S327, the activation determination section 4 outputs an activation trigger to the function control section 5 of each device that has been identified as being desired by the user 2 for manipulation. In response to the reception of this activation trigger, that device is able to begin activation.

For example, if the appearance timing of the P200 component of the event-related potential of the user 2 matches the lighting timing of the LED 142b of the microwave oven 141b, the activation determination section 4 reads a device operation in the case of selecting the microwave oven 141b from within the control data shown in FIG. 24, and outputs to the function control section 5b of the microwave oven 141b an activation trigger to "start warming". Receiving the activation trigger, the function control section 5b of the microwave oven 141b controls the output section 6b to execute a warming function.

With the above-described construction, even in the case where there are as many as several dozen and a few devices to be controlled, it is possible to perform a control by utilizing the event-related potential of an electroencephalogram at the timing as desired by the user, without long waiting for an icon to be lit.

Although the activation apparatus 22 in the above example is illustrated as a separate constituent element from the electroencephalograph 71 and the respective devices, the present invention also encompasses a construction where it is internalized in the electroencephalograph 71 or each device.

The present embodiment illustrates an example of an activation interface where the targets of manipulation are devices such as a microwave oven and an electromagnetic cooker, such that the activation interface turns On/Off of the power of each device by utilizing flickering of an LED of the device. However, the targets of control do not need to be devices; a plurality of functions which are included within a single device may be the targets of control. For example, the construction of the present embodiment would also be applicable in the case where one device has many functions, e.g., a PC.

Note that, in the case of identifying a device to be activated with a single lighting of an icon, it is necessary that the LED lighting timings of all devices are set to different timings. Moreover, when it is possible for the LED lighting timings to coincide, an event-related potential obtained by taking an arithmetic mean with respect to the LED lighting timing of each device may be utilized to perform identification of a device based on the appearance of a P200 component.

Figure 27:
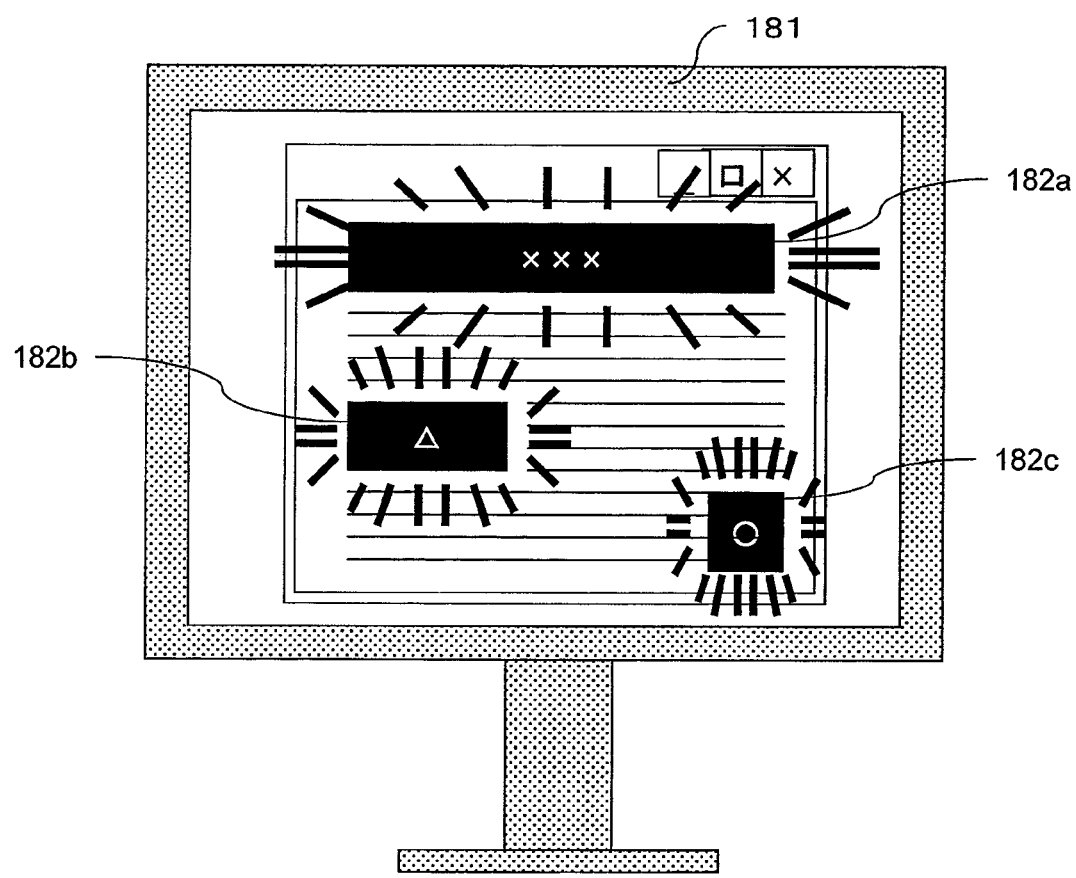
FIG. 27 A diagram showing a variant where the lighting of the LED of each device in Embodiment 4 is replaced by the lighting of a banner which is displayed on the display of a PC.

FIG. 27 shows an example where the lighting of the LED of each device of the present embodiment is replaced by the lighting of a banner which is displayed on the display of a PC.

While browsing websites on the Internet which are displayed on a PC display 181, a user may see various image advertisements. These are called banners. By clicking on a banner, it becomes possible to move the screen to a page where more detailed information is described. Thus, a banner is used as a sign indicating a move to another screen.

It is likely that a plurality of banners are displayed on the same page. For example, FIG. 27 shows three: a banner 182a, a banner 182b, and a banner 182c. Moreover, the banners are processed so that images are flickered, for example, in order to catch the eyes of the user.

The lighting of the LED of each device in the present embodiment described above can be replaced by the lighting of a banner which is displayed on the display of the PC.

For example, if a banner exists on the page being browsed that he or she wishes to know the details of, the user watches the flickering of the banner with a will of activation. Based on an electroencephalogram which is measured on the head of the user, an electroencephalogram interface system which is internalized in the PC determines the will of activation by utilizing the P200 component, and by comparing the appearance timing of the will of activation and the flicker timings of banners, the electroencephalogram interface system can determine which banner has been being watched by the user with a will of activation. By identifying the banner whose details the user wishes to know, it becomes possible to move to a page where the detailed information of the banner is described.

Thus, by utilizing flickering of banners, without any device such as a mouse, an interface can be realized which allows a desired banner to be selected and permits a move to a page that indicates the details.

INDUSTRIAL APPLICABILITY

With the electroencephalogram interface system and activation apparatus according to the present invention, it is possible to activate an electroencephalogram interface without performing any physical manipulations, and at every phase after activation of the electroencephalogram interface, e.g., selection and confirmation of a menu, manipulations via the electroencephalogram interface are possible by utilizing the electroencephalogram of a user. This system is broadly applicable in scenes where device control is required. By applying this system to an information device, for example, even in situations where the hands are full, e.g., while driving a car or holding a baby, it is possible to control that information device based only on an electroencephalogram. Moreover, since an interface manipulation is enabled without performing any physical manipulations, it is useful for devices which are characterized as hands-free, e.g., wearable devices.

The invention claimed is:

1. An electroencephalogram interface system comprising:
an electroencephalogram measurement section for measuring an electroencephalogram signal from a user,
a function control section for analyzing an event-related potential contained in the electroencephalogram signal and outputting a function control signal for controlling a function of a device based on a result of analysis,
an output section for outputting the function control signal, and
an activation apparatus for activating the electroencephalogram interface system, the activation apparatus comprising:
an activation determination section for, while the function control section of the electroencephalogram interface system is inactive, transmitting to the output section a stimulation control signal for controlling presentation and vanishing of a visual stimulation of a single-item on the output section, and, within the electroencephalogram signal acquired from the electroencephalogram measurement section, comparing a P200 component value of an event-related potential since a timing of presenting the visual stimulation as a starting point against a predetermined threshold value, and determining whether or not to output an activation trigger to the function control section based on a result of comparison; and
a stimulation attention determination section for determining whether or not the user is paying attention to the visual stimulation based on an N100 component of the event-related potential since the timing of presenting the visual stimulation as a starting point, and causing processing by the activation determination section to begin depending on a determination result, wherein,
the activation apparatus activates the electroencephalogram interface system by outputting the activation trigger to the function control section.

2. The electroencephalogram interface system of claim 1, wherein, as the P200 component value, the activation determination section compares a value of the event-related potential in a zone of 200±50 ms since the timing of presenting the visual stimulation as a starting point against the predetermined threshold value.

3. The electroencephalogram interface system of claim 1, wherein, as the P200 component value, the activation determination section compares a local maximum value, a maximum value, or a zone average value of the event-related potential in a zone of 200±50 ms since the timing of presenting the visual stimulation as a starting point against the predetermined threshold value.

4. The electroencephalogram interface system of claim 1, wherein the stimulation attention determination section instructs the activation determination section to change a method of presenting the visual stimulation based on a determination result that the user is paying attention to the visual stimulation.

5. The electroencephalogram interface system of claim 1, further comprising:
an imaging device for imaging a video and outputting a video signal; and wherein
the activation apparatus further comprises
a flicker detection section for detecting based on the video signal a subject which is flickering in the video, and based on a characteristic quantity of the subject, generating function control information which designates a function to be executed by the function control section, and outputting information indicating a lighting timing of the subject and the function control information;
the activation determination section identifies a timing of presenting the visual stimulation based on the information indicating the lighting timing, and when outputting an activation trigger to the function control section, outputs a control signal based on the function control information; and
the function control section of the electroencephalogram interface system executes a specific function based on the activation trigger and the function control information.

6. The electroencephalogram interface system of claim 5, wherein,
the flicker detection section retains a database defining a correspondence between characteristic quantities of subjects and functions to be executed by the function control section, and
by recognizing a characteristic quantity of the subject and referring to the database based on the characteristic quantity, identifies a function to be executed by the function control section and outputs the function control information.

7. The electroencephalogram interface system of claim 1, wherein:
the activation apparatus outputs the activation trigger when the stimulation attention determination section determines that the N100 component has a larger amplitude than a threshold value, and the activation determination section determines that the P200 component value is larger than the predetermined threshold value.

8. The electroencephalogram interface system of claim 1, wherein:
the activation apparatus does not output the activation trigger when the stimulation attention determination section determines that the N100 component has a larger amplitude than a threshold value, and the activation determination section determines that the P200 component value is smaller than the predetermined threshold value.

9. The electroencephalogram interface system of claim 1, wherein:
the activation apparatus does not output the activation trigger when the stimulation attention determination section determines that the N100 component has a smaller amplitude than a threshold value, and the activation determination section determines that the P200 component value is smaller than the predetermined threshold value.

10. An electroencephalogram interface system comprising:
an electroencephalogram measurement section for measuring an electroencephalogram signal from a user and a plurality of devices, and
an activation apparatus for activating at least one of the plurality of devices,
each of the plurality of devices including a function control section for outputting a function control signal for controlling a function of the device and an output section for outputting the function control signal;
the activation apparatus comprising:
a flicker timing control section for controlling the output section of each device to repeat presentation and vanishing of a visual stimulation, and outputting a determination trigger indicating a timing with which the visual stimulation is presented at any of the devices;
a storage medium for retaining determination trigger information identifying a timing of outputting the determination trigger and a device that is presenting the visual stimulation when the determination trigger is output; and
an activation determination section for, within the electroencephalogram signal acquired from the electroencephalogram measurement section, comparing a P200 component value of an event-related potential since a timing of receiving the determination trigger as a starting point against a predetermined threshold value, and based on a result of comparison, identifying the device presenting the visual stimulation based on the timing of receiving the determination trigger and the determination trigger information, and outputting an activation trigger to the function control section of the identified device; and
a stimulation attention determination section for determining whether or not the user is paying attention to the visual stimulation based on an N100 component of the event-related potential since the timing of presenting the visual stimulation as a starting point, and causing processing by the activation determination section to begin depending on a determination result, wherein,
the activation apparatus activates the device identified by the activation determination section by outputting the activation trigger.

11. An activation method for activating an electroencephalogram interface system,
the electroencephalogram interface system including
an electroencephalogram measurement section for measuring an electroencephalogram signal from a user,
a function control section for analyzing an event-related potential contained in the electroencephalogram signal and outputting a function control signal for controlling a function of a device based on a result of analysis, and
an output section for outputting the function control signal,
the activation method comprising the steps of:
while the function control section of the electroencephalogram interface system is inactive, transmitting to the output section a stimulation control signal for controlling presentation and vanishing of a visual stimulation on a single-item on the output section;
determining whether or not the user is paying attention to the visual stimulation based on an N100 component of the event-related potential since a timing of presenting the visual stimulation as a starting point;
based on a determination result, comparing a P200 component value of an event-related potential since the timing of presenting the visual stimulation as a starting point, within the electroencephalogram signal acquired from the electroencephalogram measurement section, to be compared against a predetermined threshold value;
determining whether or not to output an activation trigger to the function control section based on a result of comparison; and
activating the electroencephalogram interface system by outputting the activation trigger to the function control section when it is determined to output the activation trigger.

12. A non-transitory computer-readable medium storing a computer program that is executed by a computer of an activation apparatus incorporated in an electroencephalogram interface system,
the electroencephalogram interface system including
an electroencephalogram measurement section for measuring an electroencephalogram signal from a user,
a function control section for analyzing an event-related potential contained in the electroencephalogram signal and outputting a function control signal for controlling a function of a device based on a result of analysis, and
an output section for outputting the function control signal, wherein,
the computer program causes the computer of the activation apparatus to execute:
while the function control section of the electroencephalogram interface system is inactive, transmitting to the output section a stimulation control signal for controlling presentation and vanishing of a visual stimulation on a single-item on the output section;
determining whether or not the user is paying attention to the visual stimulation based on an N100 component of the event-related potential since a timing of presenting the visual stimulation as a starting point;
based on a determination result, comparing a P200 component value of an event-related potential since the timing of presenting the visual stimulation as a starting point, within the electroencephalogram signal acquired from the electroencephalogram measurement section, against a predetermined threshold value;
determining whether or not to output an activation trigger to the function control section based on a result of comparison; and
activating the electroencephalogram interface system by outputting the activation trigger to the function control section when it is determined to output the activation trigger.

* * * * *